(12) United States Patent
Taylor et al.

(10) Patent No.: US 12,127,969 B2
(45) Date of Patent: Oct. 29, 2024

(54) THERMAL SYSTEM WITH GRAPHICAL USER INTERFACE

(71) Applicant: Stryker Corporation, Kalamazoo, MI (US)

(72) Inventors: Gregory S. Taylor, Kalamazoo, MI (US); Marco Constant, Portage, MI (US); Christopher John Hopper, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 1415 days.

(21) Appl. No.: 16/222,004

(22) Filed: Dec. 17, 2018

(65) Prior Publication Data

US 2019/0192339 A1 Jun. 27, 2019

Related U.S. Application Data

(60) Provisional application No. 62/610,362, filed on Dec. 26, 2017.

(51) Int. Cl.
*A61F 7/00* (2006.01)
*A61B 5/00* (2006.01)
(Continued)

(52) U.S. Cl.
CPC .............. *A61F 7/0085* (2013.01); *A61B 5/01* (2013.01); *A61B 5/4836* (2013.01);
(Continued)

(58) Field of Classification Search
CPC ...... A61F 7/0053; A61F 7/007; A61F 7/0085; A61F 2007/0054; A61F 2007/0086;
(Continued)

(56) References Cited

U.S. PATENT DOCUMENTS 4,884,072 A 7/1989 French et al.
6,245,347 B1 6/2001 Zhang et al.
(Continued)

OTHER PUBLICATIONS

Gaymar Medi-Therm III, Hyper/Hypothermia Machine Ref MTA7912 Service Manual, Nov. 2009.
(Continued)

*Primary Examiner* — Kaitlyn E Smith
*Assistant Examiner* — Bradford C. Blaise
(74) *Attorney, Agent, or Firm* — Warner Norcross + Judd LLP

(57) ABSTRACT

A thermal control unit for controlling a patient's temperature includes a fluid outlet for delivering temperature-controlled fluid to a patient, a pump, a heat exchanger, a controller, and a user interface that displays a graph of patient temperature readings over time. The user interface also displays one or more event icons on the graph at locations corresponding to the time at which events associated with the event icons occurred. In some embodiments, the graph is displayed on a touch screen adapted to allow a user set maximum and minimum permissible temperatures for the fluid by touching areas of the graphs and/or by drawing on certain areas of the graph. An image of a human body having different zones may also be displayed on the user interface along with information pertaining to the thermal therapy being applied to the corresponding zones of the patient's body.

19 Claims, 10 Drawing Sheets

(51) Int. Cl.
*A61B 5/01* (2006.01)
*G06F 3/0481* (2022.01)
*G06F 3/0488* (2022.01)

(52) U.S. Cl.
CPC ............ *A61F 7/0053* (2013.01); *A61F 7/007* (2013.01); *G06F 3/0481* (2013.01); *G06F 3/0488* (2013.01); *A61F 2007/0054* (2013.01); *A61F 2007/0086* (2013.01); *A61F 2007/0093* (2013.01)

(58) Field of Classification Search
CPC . A61F 2007/0093; A61B 5/01; A61B 5/4836; G06F 3/048; G06F 3/0481; G06F 3/0488
See application file for complete search history.

(56) References Cited

U.S. PATENT DOCUMENTS

| | | | |
|---|---|---|---|
| 6,830,581 B2 | 12/2004 | Magers | |
| 6,840,955 B2 | 1/2005 | Ein | |
| 8,647,374 B2 | 2/2014 | Koewler | |
| 9,474,847 B2 | 10/2016 | Bonutti et al. | |
| 9,830,646 B1* | 11/2017 | Wasser | G06F 3/0484 |
| 2002/0058976 A1 | 5/2002 | Lee | |
| 2003/0163183 A1* | 8/2003 | Carson | A61M 1/369 |
| | | | 607/104 |
| 2005/0283387 A1* | 12/2005 | Donoghue | G16H 70/20 |
| | | | 705/2 |
| 2006/0195168 A1 | 8/2006 | Dunbar et al. | |
| 2008/0228055 A1* | 9/2008 | Sher | A61B 5/14532 |
| | | | 600/365 |
| 2008/0255641 A1 | 10/2008 | Ellis | |
| 2008/0281297 A1 | 11/2008 | Pesach et al. | |
| 2009/0099629 A1* | 4/2009 | Carson | A61F 7/00 |
| | | | 607/96 |
| 2009/0112298 A1 | 4/2009 | Jusiak et al. | |
| 2009/0131835 A1* | 5/2009 | Voorhees | A61B 5/11 |
| | | | 600/595 |
| 2009/0254159 A1 | 10/2009 | Stormby | |
| 2011/0304466 A1* | 12/2011 | Bair, III | G06F 3/0484 |
| | | | 62/126 |
| 2014/0200487 A1 | 7/2014 | Ramdas et al. | |
| 2014/0343639 A1* | 11/2014 | Hopper | A61F 7/0085 |
| | | | 607/104 |
| 2016/0227929 A1 | 8/2016 | Paul et al. | |
| 2017/0228900 A1* | 8/2017 | Okabe | G06F 17/18 |
| 2017/0348144 A1 | 12/2017 | Taylor et al. | |
| 2017/0348449 A1 | 12/2017 | Ward et al. | |
| 2018/0014967 A1 | 1/2018 | Taylor | |
| 2018/0042762 A1 | 2/2018 | Galer | |
| 2018/0042763 A1 | 2/2018 | Galer et al. | |
| 2018/0098878 A1 | 4/2018 | Kostic et al. | |
| 2018/0140459 A1 | 5/2018 | Taylor et al. | |
| 2018/0214301 A1 | 8/2018 | Fojtik et al. | |
| 2018/0280191 A1 | 10/2018 | Taylor et al. | |
| 2019/0110759 A1* | 4/2019 | Tanishima | A61B 5/742 |
| 2019/0159739 A1* | 5/2019 | Shah | A61B 5/01 |
| 2019/0328598 A1* | 10/2019 | Mangiardi | H05B 3/52 |

OTHER PUBLICATIONS

Altrix Precision Temperature Management System Stryker Operations Manuel, Dec. 2016.
Sorin Group, Heater-Cooling System 3T, Operating Instructions, 2015.
Arctic Sun 5000 Service Manual by Medivance, Inc., 2010-2011.
"DigniCap How it Works—The Intelligent Scalp Cooling System", Dignitana Inc., 2017.
Temperature control in critically ill patients with a novel esophageal cooling device; a case series, BMS Anesthesiology, Ahmed F. Hegazy, Danielle M. Lapierre, Ron Butler and Eyad Althenayan, 2015.
Specification and Drawings as filed for commonly assigned U.S. Appl. No. 62/525,353, filed Jun. 27, 2017 entitled Patient Support Systems and Methods for Assisting Caregivers With Patient Care.
Specification and Drawings as filed for commonly assigned U.S. Appl. No. 62/525,363, filed Jun. 27, 2017 entitled Patient Support Systems and Methods for Assisting Caregivers With Patient Care.

* cited by examiner

THERMAL SYSTEM WITH GRAPHICAL USER INTERFACE

CROSS-REFERENCE TO RELATED APPLICATIONS

This application claims priority to U.S. provisional patent application Ser. No. 62/610,362 filed Dec. 26, 2017, by inventor Gregory S. Taylor and entitled THERMAL SYSTEM WITH GRAPHICAL USER INTERFACE, the complete disclosure of which is incorporated herein by reference.

BACKGROUND

The present disclosure relates to a thermal control system for controlling the temperature of circulating fluid that is delivered to one or more thermal pads positioned in contact with a patient.

Thermal control systems are known in the art for controlling the temperature of a patient by providing a thermal control unit that supplies temperature-controlled fluid to one or more thermal pads or catheters positioned in contact with a patient. The thermal control unit includes one or more heat exchangers for controlling the temperature of the fluid and a pump that pumps the temperature-controlled fluid to the pad(s) and/or catheter. After passing through the pad(s) and/or catheter, the fluid is returned to the thermal control unit where any necessary adjustments to the temperature of the returning fluid are made before being pumped back to the pad(s) and/or catheter. In some instances, the temperature of the fluid is controlled to a static target temperature, while in other instances the temperature of the fluid is varied as necessary in order to automatically effectuate a target patient temperature.

Thermal control units typically include a user interface adapted to allow the user to input information for using the thermal control unit, as well as for displaying information useful to the user of the thermal control unit.

SUMMARY

The present disclosure is directed to an improved thermal control unit that improves upon the user interface in one or more manners, including, but not limited to, displaying thermal therapy treatment information in a more concise and integrated fashion, allowing users to achieve easier and greater control over the thermal control unit, controlling the thermal therapy device with a greater degree of granularity, and providing zone-specific information to the user. Still other improved aspects of the thermal control system disclosed herein will be apparent to those skilled in the art in light of the following written description.

According to one embodiment of the present disclosure a thermal control unit is provided for controlling a patient's temperature that includes a fluid outlet, a fluid inlet, a pump, a heat exchanger, a fluid temperature sensor, a patient temperature sensor port, a controller, and a user interface. The fluid outlet couples to a fluid supply line and the fluid inlet couples to a fluid return line. The circulation channel fluidly couples the fluid outlet and the fluid inlet. The pump circulates the fluid through the circulation channel from the fluid inlet to the fluid outlet. The heat exchanger adds or removes heat from the fluid circulating in the circulation channel. The patient temperature sensor port is adapted receive patient temperature readings from a patient temperature sensor. The controller controls the heat exchanger in order to control the patient's temperature, and the user interface is adapted to display patient temperature readings on a graph having a time axis and a temperature axis. The user interface is also adapted to display an event icon on the graph. The event icon corresponds to an event occurring at an event time and is related to the thermal therapy. The event icon is displayed at a position on the graph along the time axis that corresponds to the event time.

According to other aspects of the present disclosure, the user interface includes a touch screen display and both the event icon and the graph are displayed on the touch screen display.

In some embodiments, the user interface is adapted to provide further information about the event when the event icon is touched by a user. The event may be one or more of the following: a medication delivered to the patient; a detection of patient shivering; a sedation of the patient; a changing of a thermal pad coupled to the fluid supply line and fluid return line; an adjustment of a thermal pad coupled to the fluid supply line and fluid return line; a change in location of the patient temperature sensor; a flushing of the patient's body adjacent the patient temperature sensor; a performance of maintenance on the thermal control unit; an error detected by the controller; an alert issued by the controller; and/or another type of event.

In some instances, the controller detects an occurrence of the event and automatically displays the event icon on the graph after detecting the event occurrence, while in other instances the user interface displays the event icon on the graph in response to a user manually entering information regarding the event via the user interface.

When manually entering event information, the user interface may be adapted to allow a user to enter the event time by touching a position along the time axis corresponding to the event time.

The user interface is also adapted to display a plurality of event icons on the graph, each event icon being displayed at a position along the time axis corresponding to the time of the underlying event associated with the event icon.

Additional information may also be displayed on the graph, such as, but not limited to, fluid temperature readings from the fluid temperature sensor, a patient target temperature, a heart rate of the patient, a respiration rate of the patient, a potassium level of the patient, a blood pressure of the patient, and/or other information.

In some embodiments, the user interface is adapted to allow a user to touch a first location on the graph along the temperature axis to set a maximum temperature of the fluid, and to touch a second location along the temperature axis to set a minimum temperature of the fluid. The controller controls the heat exchanger such that a temperature of the circulating fluid does not exceed the maximum and minimum temperatures.

The thermal control unit, in some embodiments, includes a user interface having a filter control that, when selected, filters one or more selected event icons such that the user interface does not display any filtered event icons.

According to another embodiment of the present disclosure, a thermal control unit for controlling a patient's temperature during thermal therapy is provided. The thermal control unit includes a fluid outlet, a fluid inlet, a pump, a heat exchanger, a fluid temperature sensor, a patient temperature sensor port, a controller, and a user interface. The fluid outlet couples to a fluid supply line and the fluid inlet couples to a fluid return line. The circulation channel fluidly couples the fluid outlet and the fluid inlet. The pump circulates the fluid through the circulation channel from the fluid inlet to the fluid outlet. The heat exchanger adds or removes heat from the fluid circulating in the circulation channel. The patient temperature sensor port is adapted receive patient temperature readings from a patient temperature sensor. The controller controls the heat exchanger in order to control the patient's temperature, and the user interface is adapted to display patient temperature readings on a graph having a time axis and a temperature axis. The user interface is further adapted to allow a user to touch a first location on the graph along the temperature axis to set a maximum permissible temperature of the fluid, and to touch a second location along the temperature axis to set a minimum permissible temperature of the fluid. The controller controls the heat exchanger such that a temperature of the circulating fluid does not exceed the maximum and minimum permissible temperatures.

According to other aspects, the user interface is further adapted to determine a first time on the time axis corresponding to the first location and a second time on the time axis corresponding to the second location. Thereafter, the controller controls the heat exchanger such that the temperature of the circulating fluid does not exceed the maximum permissible temperature at the first time and does not exceed the minimum temperature at the second time.

In some embodiments, the user interface is adapted to allow a user to draw a first line on the graph defining a plurality of maximum temperatures at a first plurality of times, and to draw a second line on the graph defining a plurality of minimum temperatures at a second plurality of times. The controller then controls the heat exchanger such that the temperature of the circulating fluid does not exceed the plurality of maximum temperatures at the first plurality of times and does not exceed the plurality of minimum temperatures at the second plurality of times.

The user interface is further adapted, in some embodiments, to allow a user to touch a third location on the graph along the temperature axis to set a target temperature for the patient.

In some embodiments, the user interface is further adapted to allow a user to draw a first line on the graph defining a plurality of patient target temperatures at a plurality of times. In response, the controller controls the heat exchanger such that the temperature of the patient is controlled to match the plurality of patient target temperatures at the plurality of times.

According to another embodiment of the present disclosure, a thermal control unit for controlling a patient's temperature during thermal therapy is provided. The thermal control unit includes first and second fluid inlets and first and second fluid outlets, a circulation channel, a pump, a heat exchanger, a first inlet fluid temperature sensor, a second inlet fluid temperature sensor, an outlet fluid temperature sensor, a controller, and a user interface. The first fluid outlet and first fluid inlet are adapted to supply and receive, respectively, temperature-controlled fluid for a first zone of a patient's body. The second fluid outlet and second fluid inlet are adapted to supply and receive, respectively, temperature-controlled fluid for a second zone of a patient's body. The circulation channel fluidly couples the first and second fluid inlets to the first and second fluid outlets. The pump circulates fluid through the circulation channel from the first and second fluid inlets to the first and second fluid outlets. The heat exchanger adds or removes heat from the fluid circulating in the circulation channel. The first and second inlet temperature sensors sense temperatures of the fluid returning from the first and second fluid inlets, respectively. The controller controls the heat exchanger in order to control the patient's temperature. The user interface is adapted to display a first set of information relating to the patient's first zone and a second set of information relating to the patient's second zone.

According to other aspects, the first set of information includes information derived from the first inlet fluid temperature sensor and the second set of information includes information derived from the second inlet fluid temperature sensor.

The user interface may also be adapted to display an image of a human body and locations of the first and second zones on the human body image. When the user interface includes a touch screen, the user interface is adapted to display the first set of information when a user touches the first zone of the human body image on the touch screen and to display the second set of information when the user touches the second zone of the human body image on the touch screen.

In some embodiments, the first set of information includes an indication of a first amount of heat transfer to or from the patient's first zone, and the second set of information includes an indication of a second amount of heat transfer to or from the patient's second zone.

The thermal control unit may further comprise a first patient temperature sensor port adapted to receive patient temperature readings from a first patient temperature sensor positioned in the first zone and a second patient temperature sensor port adapted to receive patient temperature readings from a second patient temperature sensor positioned in the second zone. The first set of information includes information derived from the first patient temperature sensor and the second set of information includes information derived from the second patient temperature sensor.

In some embodiments, the user interface is adapted to display first patient temperature readings from the first patient temperature sensor on a first graph having a first time axis and a first temperature axis, and to display second patient temperature readings from the second patient temperature sensor on a second graph having a second time axis and a second temperature axis.

When a touch screen is included, the user interface may be adapted to allow a user to control a first thermal therapy parameter associated with the first zone by touching on the first zone of the human body image, and to allow a user to control a second thermal therapy parameter associated with the second zone by touching on the second zone of the human body image. In some embodiments, the first thermal therapy parameter is a limit on a temperature of the fluid delivered to the first zone of the patient's body and the second thermal therapy parameter is a limit on a temperature of the fluid delivered to the second zone of the patient's body. Other parameters may also be controlled via the touch screen.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
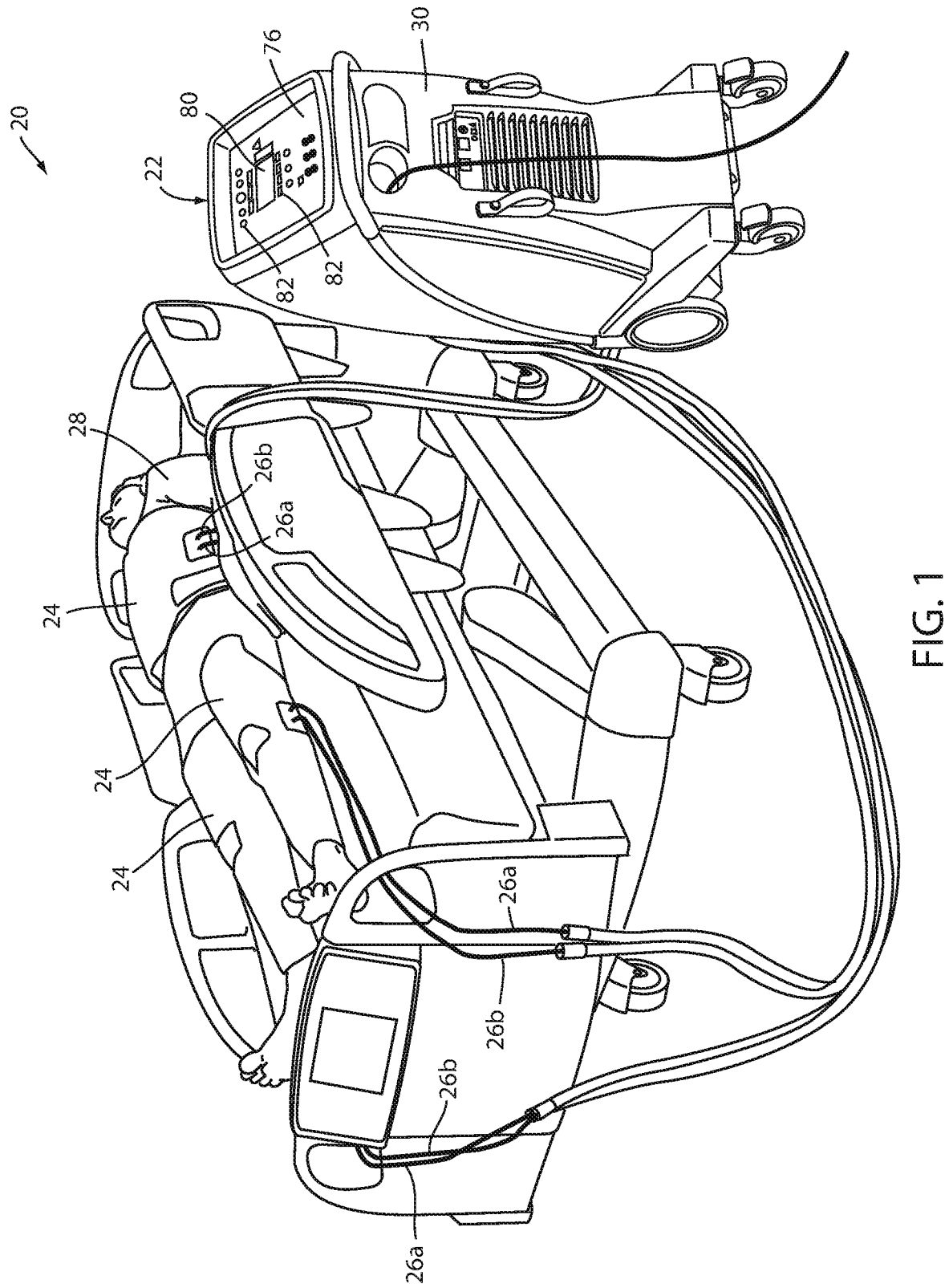
FIG. 1 is a perspective view of a thermal control system according to one aspect of the present disclosure shown applied to a patient on a patient support apparatus.

A thermal control system 20 according to one embodiment of the present disclosure is shown in FIG. 1. Thermal control system 20 is adapted to control the temperature of a patient 28, which may involve raising, lowering, and/or maintaining the patient's temperature. Thermal control system 20 includes a thermal control unit 22 coupled to one or more thermal therapy devices 24. The thermal therapy devices 24 are illustrated in FIG. 1 to be thermal pads, but it will be understood that thermal therapy devices 24 may take on other forms, such as, but not limited to, blankets, vests, patches, caps, catheters, or other structures that receive temperature-controlled fluid. For purposes of the following written description, thermal therapy devices 24 will be referred to as thermal pads 24, but it will be understood by those skilled in the art that this terminology is used merely for convenience and that the phrase "thermal pad" is intended to cover all of the different variations of thermal therapy devices 24 mentioned above (e.g. blankets, vests, patches, caps, catheters, etc.) and variations thereof.

Thermal control unit 22 is coupled to thermal pads 24 via a plurality of hoses 26. Thermal control unit 22 delivers temperature-controlled fluid (such as, but not limited to, water or a water mixture) to the thermal pads 24 via the fluid supply hoses 26a. After the temperature-controlled fluid has passed through thermal pads 24, thermal control unit 22 receives the temperature-controlled fluid back from thermal pads 24 via the return hoses 26b.

In the embodiment of thermal control system 20 shown in FIG. 1, three thermal pads 24 are used in the treatment of patient 28. A first thermal pad 24 is wrapped around a patient's torso, while second and third thermal pads 24 are wrapped, respectively, around the patient's right and left legs. Other configurations can be used and different numbers of thermal pads 24 may be used with thermal control unit 22, depending upon the number of inlet and outlet ports that are included with thermal control unit 22. By controlling the temperature of the fluid delivered to thermal pads 24 via supply hoses 26a, the temperature of the patient 28 can be controlled via the close contact of the pads 24 with the patient 28 and the resultant heat transfer therebetween.

Figure 2:
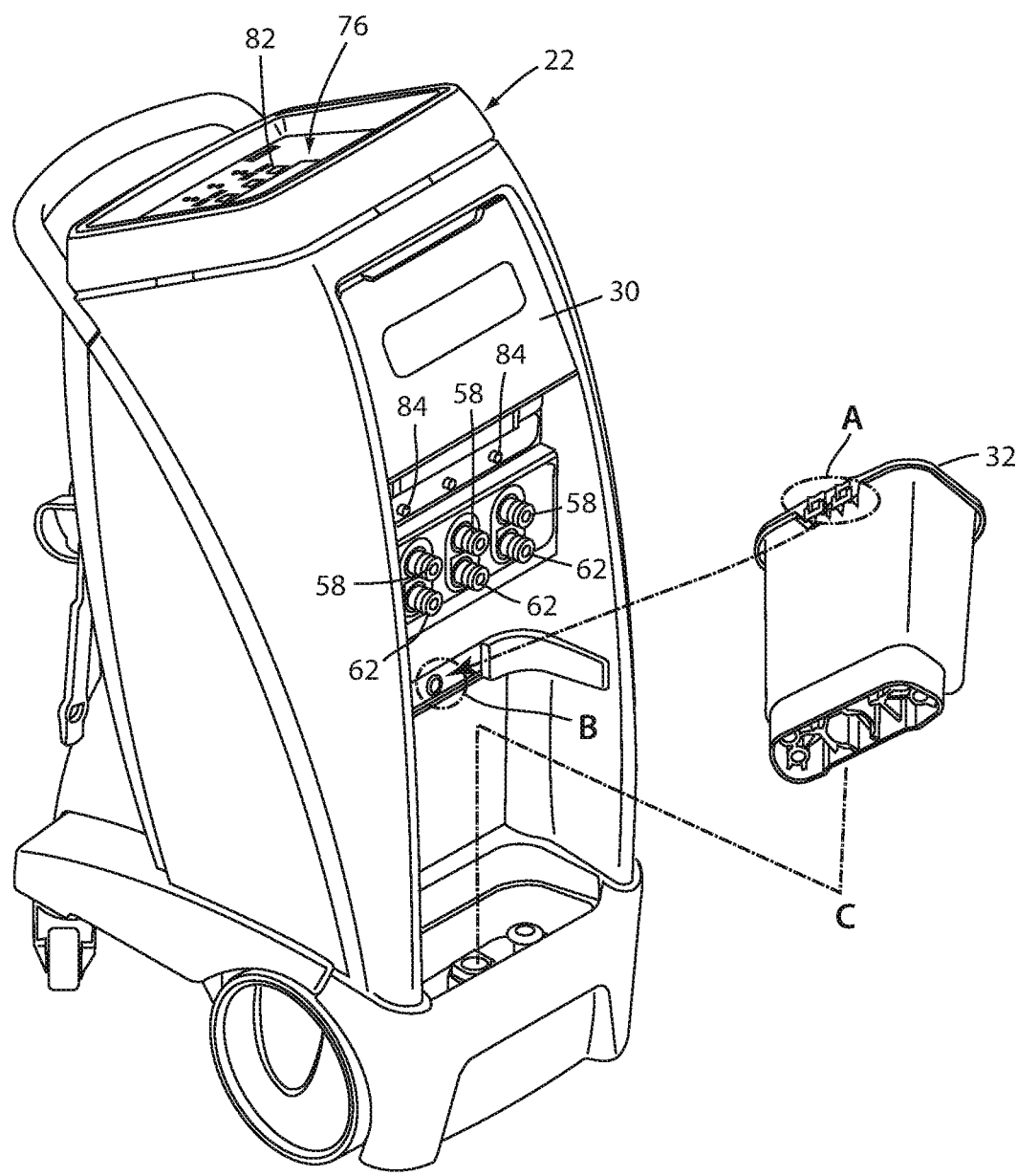
FIG. 2 is a perspective view of a thermal control unit of the thermal control system of FIG. 1.

As shown more clearly in FIG. 2, thermal control unit 22 includes a main body 30 to which a removable reservoir 32 may be coupled and uncoupled. Removable reservoir 32 is configured to hold the fluid that is to be circulated through thermal control unit 22 and the one or more thermal pads 24. By being removable from thermal control unit 22, reservoir 32 can be easily carried to a sink or faucet for filling and/or dumping of the water or other fluid. This allows users of thermal control system 20 to more easily fill thermal control unit 22 prior to its use, as well as to drain thermal control unit 22 after use.

Figure 3:
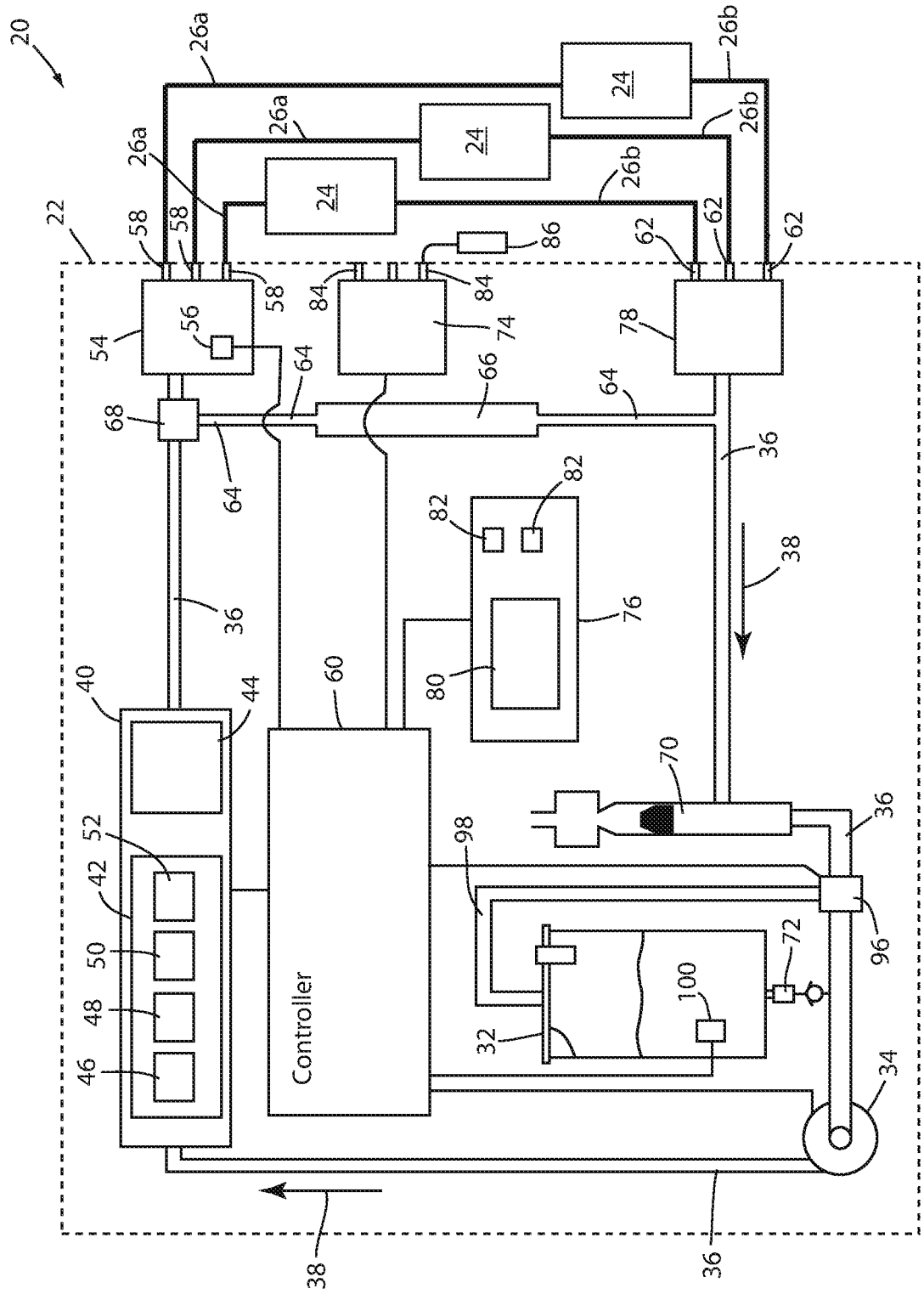
FIG. 3 is a block diagram of a first embodiment of the thermal control system of FIG. 1.

As shown in FIG. 3, thermal control unit 22 includes a pump 34 for circulating fluid through a circulation channel 36. Pump 34, when activated, circulates the fluid through circulation channel 36 in the direction of arrows 38 (clockwise in FIG. 3). Starting at pump 34 the circulating fluid first passes through a heat exchanger 40 that adjusts, as necessary, the temperature of the circulating fluid. Heat exchanger 40 may take on a variety of different forms. In some embodiments, heat exchanger 40 is a thermoelectric heater and cooler. In the embodiment shown in FIG. 3, heat exchanger 40 includes a chiller 42 and a heater 44. Further, in the embodiment shown in FIG. 3, chiller 42 is a conventional vapor-compression refrigeration unit having a compressor 46, a condenser 48, an evaporator 50, an expansion valve (not shown), and a fan 52 for removing heat from the compressor 46. Other types of chillers and/or heaters may be used.

After passing through heat exchanger 40, the circulating fluid is delivered to an outlet manifold 54 having an outlet temperature sensor 56 and a plurality of outlet ports 58. Temperature sensor 56 is adapted to detect a temperature of the fluid inside of outlet manifold 54 and report it to a controller 60. Outlet ports 58 are coupled to supply hoses 26a. Supply hoses 26a are coupled, in turn, to thermal pads 24 and deliver temperature-controlled fluid to the thermal pads 24. The temperature-controlled fluid, after passing through the thermal pads 24, is returned to thermal control unit 22 via return hoses 26b. Return hoses 26b couple to a plurality of inlet ports 62. Inlet ports 62 are fluidly coupled to an inlet manifold 78 inside of thermal control unit 22.

Thermal control unit 22 also includes a bypass line 64 fluidly coupled to outlet manifold 54 and inlet manifold 78 (FIG. 3). Bypass line 64 allows fluid to circulate through circulation channel 36 even in the absence of any thermal pads 24 or hoses 26a being coupled to any of outlet ports 58. In the illustrated embodiment, bypass line 64 includes an optional filter 66 that is adapted to filter the circulating fluid.

If included, filter 66 may be a particle filter adapted to filter out particles within the circulating fluid that exceed a size threshold, or filter 66 may be a biological filter adapted to purify or sanitize the circulating fluid, or it may be a combination of both. In some embodiments, filter 66 is constructed and/or positioned within thermal control unit 22 in any of the manners disclosed in commonly assigned U.S. patent application Ser. No. 62/404,676 filed Oct. 11, 2016, by inventors Marko Kostic et al. and entitled THERMAL CONTROL SYSTEM, the complete disclosure of which is incorporated herein by reference.

The flow of fluid through bypass line 64 is controllable by way of a bypass valve 68 positioned at the intersection of bypass line 64 and outlet manifold 54 (FIG. 3). When open, bypass valve 68 allows fluid to flow through circulation channel 36 to outlet manifold 54, and from outlet manifold 54 to the connected thermal pads 24. When closed, bypass valve 68 stops fluid from flowing to outlet manifold 54 (and thermal pads 24) and instead diverts the fluid flow along bypass line 64. In some embodiments, bypass valve 68 may be controllable such that selective portions of the fluid are directed to outlet manifold 54 and along bypass line 64. In some embodiments, bypass valve 68 is controlled in any of the manners discussed in commonly assigned U.S. patent application Ser. No. 62/610,319, filed Dec. 26, 2017, by inventors Gregory Taylor et al. and entitled THERMAL SYSTEM WITH OVERSHOOT REDUCTION, the complete disclosure of which is incorporated herein by reference.

The incoming fluid flowing into inlet manifold 78 from inlet ports 62 and/or bypass line 64 travels back toward pump 34 and into an air remover 70. Air remover 70 includes any structure in which the flow of fluid slows down sufficiently to allow air bubbles contained within the circulating fluid to float upwardly and escape to the ambient surroundings. In some embodiments, air remover 70 is constructed in accordance with any of the configurations disclosed in commonly assigned U.S. patent application Ser. No. 15/646,847 filed Jul. 11, 2017, by inventor Gregory S. Taylor and entitled THERMAL CONTROL SYSTEM, the complete disclosure of which is hereby incorporated herein by reference. After passing through air remover 70, the circulating fluid flows past a valve 72 positioned beneath fluid reservoir 32. Fluid reservoir 32 supplies fluid to thermal control unit 22 and circulation channel 36 via valve 72, which may be a conventional check valve, or other type of valve, that automatically opens when reservoir 32 is coupled to thermal control unit 22 and that automatically closes when reservoir 32 is decoupled from thermal control unit 22 (see FIG. 2). After passing by valve 72, the circulating fluid travels to pump 34 and the circuit is repeated.

Controller 60 of thermal control unit 22 is contained within main body 30 of thermal control unit 22 and is in electrical communication with pump 34, heat exchanger 40, outlet temperature sensor 56, bypass valve 68, a patient temperature module 74, and a user interface 76. Controller 60 includes any and all electrical circuitry and components necessary to carry out the functions and algorithms described herein, as would be known to one of ordinary skill in the art. Generally speaking, controller 60 may include one or more microcontrollers, microprocessors, and/or other programmable electronics that are programmed to carry out the functions described herein. It will be understood that controller 60 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in thermal control unit 22, or they may reside in a common location within thermal control unit 22. When physically distributed, the components may communicate using any suitable serial or parallel communication protocol, such as, but not limited to, CAN, LIN, Firewire, I-squared-C, RS-232, RS-465, universal serial bus (USB), etc.

User interface 76, which may be implemented as a control panel or in other manners, allows a user to operate thermal control unit 22. User interface 76 communicates with controller 60 and includes a display 80 and a plurality of dedicated controls 82. Display 80 may be implemented as a touch screen, or, in some embodiments, as a non-touch-sensitive display. Dedicated controls 82 may be implemented as buttons, switches, dials, or other dedicated structures. In any of the embodiments, one or more of the functions carried out by a dedicated control 82 may be replaced or supplemented with a touch screen control that is activated when touched by a user. Alternatively, in any of the embodiments, one or more of the controls that are carried out via a touch screen can be replaced or supplemented with a dedicated control 82 that carries out the same function when activated by a user.

Through either dedicated controls 82 and/or a touch screen display (e.g. display 80), user interface 76 enables a user to turn thermal control unit 22 on and off, select a mode of operation, select a target temperature for the fluid delivered to thermal pads 24, select a patient target temperature, and control other aspects of thermal control unit 22. In some embodiments, user interface 76 may include a pause/event control, a medication control, and/or an automatic temperature adjustment control that operate in accordance with the pause event control 66b, medication control 66c, and automatic temperature adjustment control 66d disclosed in commonly assigned U.S. patent application Ser. No. 62/577,772 filed on Oct. 27, 2017, by inventors Gregory Taylor et al. and entitled THERMAL SYSTEM WITH MEDICATION INTERACTION, the complete disclosure of which is incorporated herein by reference. Such controls may be activated as touch screen controls or dedicated controls 82.

In those embodiments where user interface 76 allows a user to select from different modes for controlling the patient's temperature, the different modes include, but are not limited to, a manual mode and an automatic mode, both of which may be used for cooling and heating the patient. In the manual mode, a user selects a target temperature for the fluid that circulates within thermal control unit 22 and that is delivered to thermal pads 24. Thermal control unit 22 then makes adjustments to heat exchanger 40 in order to ensure that the temperature of the fluid exiting supply hoses 26a is at the user-selected temperature.

Another one of the modes is an automatic mode. When the user selects the automatic mode, the user selects a target patient temperature, rather than a target fluid temperature. After selecting the target patient temperature, controller 60 makes automatic adjustments to the temperature of the fluid in order to bring the patient's temperature to the desired patient target temperature. In this mode, the temperature of the circulating fluid may vary as necessary in order to bring about the target patient temperature.

In order to carry out the automatic mode, thermal control unit 22 utilizes patient temperature module 74. Patient temperature module 74 includes one or more patient temperature sensor ports 84 (FIGS. 2 & 3) that are adapted to receive one or more conventional patient temperature sensors or probes 86. The patient temperature sensors 86 may be any suitable patient temperature sensor that is able to sense the temperature of the patient at the location of the sensor. In one embodiment, the patient temperature sensors are conventional Y.S.I. 400 probes marketed by YSI Incorporated of Yellow Springs, Ohio, or probes that are YSI 400 compliant. In other embodiments, different types of sensors may be used with thermal control unit 22. Regardless of the specific type of patient temperature sensor used in thermal control system 20, each temperature sensor 86 is connected to a patient temperature sensor port 84 positioned on thermal control unit 22. Patient temperature sensor ports 84 are in electrical communication with controller 60 and provide current temperature readings of the patient's temperature.

Controller 60, in some embodiments, controls the temperature of the circulating fluid using closed-loop feedback from temperature sensor 56. That is, controller 60 determines (or receives) a target temperature of the fluid, compares it to the measured temperature from sensor 56, and issues a command to heat exchanger 40 that seeks to decrease the difference between the desired fluid temperature and the measured fluid temperature. In some embodiments, the difference between the fluid target temperature and the measured fluid temperature is used as an error value that is input into a conventional Proportional, Integral, Derivative (PID) control loop. That is, controller 60 multiplies the fluid temperature error by a proportional constant, determines the derivative of the fluid temperature error over time and multiplies it by a derivative constant, and determines the integral of the fluid temperature error over time and multiplies it by an integral constant. The results of each product are summed together and converted to a heating/cooling command that is fed to heat exchanger 40 and tells heat exchanger 40 whether to heat and/or cool the circulating fluid and how much heating/cooling power to use.

Figure 4:
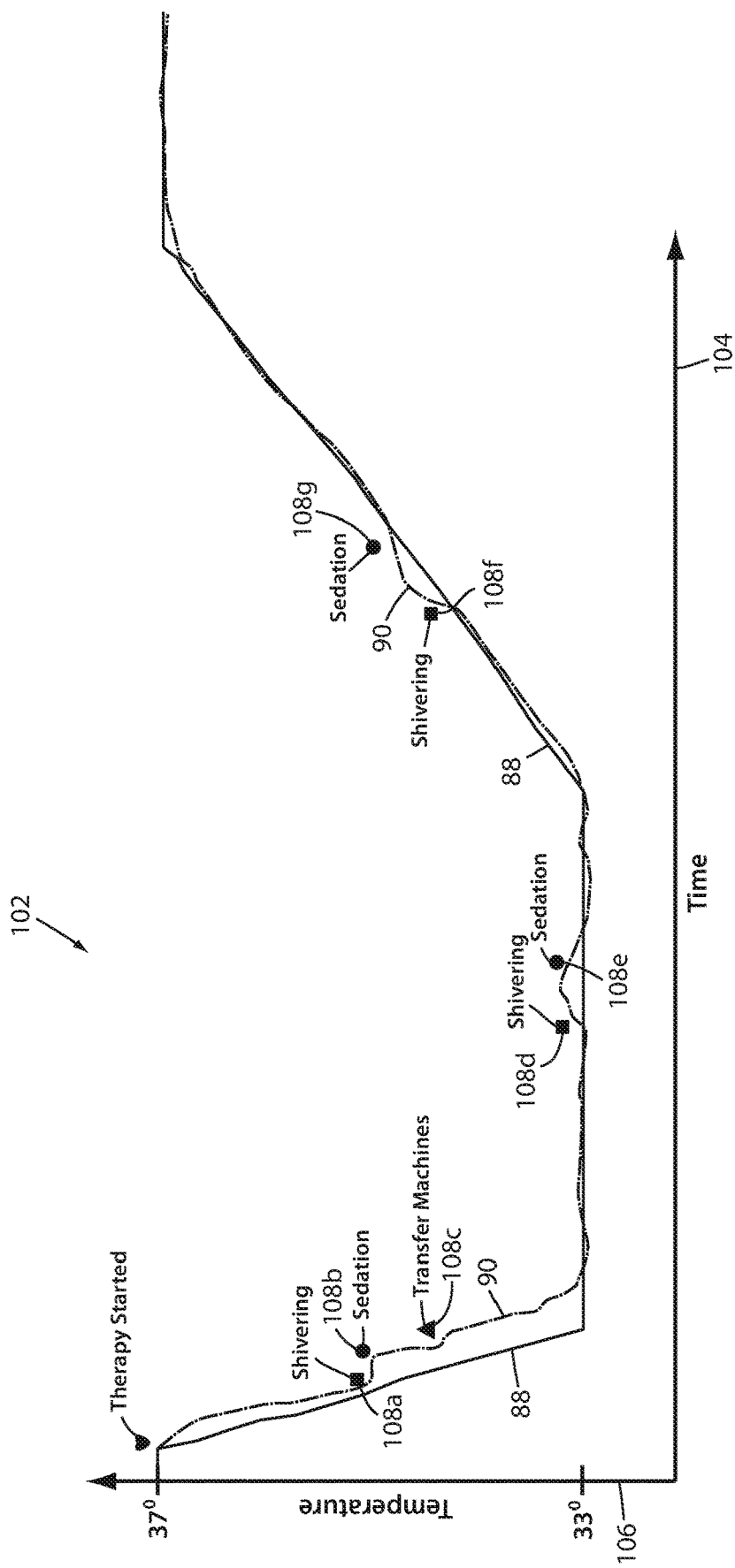
FIG. 4 is an illustrative graph displayable on a user interface of the thermal control unit showing a patient's actual temperature, the patient's target temperature, and a plurality of events.

When thermal control unit 22 is operating in the automatic mode, controller 60 may use a second closed-loop control loop that determines the difference between a patient target temperature 88 and a measured patient temperature 90 (FIG. 4). The patient target temperature 88 is input by a user of thermal control unit 22 using user interface 76. Measured patient temperature 90 comes from a patient temperature sensor 86 coupled to one of patient temperature sensor ports 84 (FIG. 3). Controller 60 determines the difference between the patient target temperature 88 and the measured patient temperature 90 and, in some embodiments, uses the resulting patient temperature error value as an input into a conventional PID control loop. As part of the PID loop, controller 60 multiplies the patient temperature error by a proportional constant, multiplies a derivative of the patient temperature error over time by a derivative constant, and multiplies an integral of the patient temperature error over time by an integral constant. The three products are summed together and converted to a target fluid temperature value. The target fluid temperature value is then fed to the first control loop discussed above, which uses it to compute a fluid temperature error.

It will be understood by those skilled in the art that other types of control loops may be used. For example, controller 60 may utilize one or more PI loops, PD loops, and/or other types of control equations. In some embodiments, the coefficients used with the control loops may be varied by controller 60 depending upon the patient's temperature reaction to the thermal therapy, among other factors. One example of such dynamic control loop coefficients is disclosed in commonly assigned U.S. patent application Ser. No. 62/577,772 filed on Oct. 27, 2017, by inventors Gregory Taylor et al. and entitled THERMAL SYSTEM WITH MEDICATION INTERACTION, the complete disclosure of which is incorporated herein by reference.

Regardless of the specific control loop utilized, controller 60 implements the loop(s) multiple times a second in at least one embodiment, although it will be understood that this rate may be varied widely. After controller 60 has output a heat/cool command to heat exchanger 40, controller 60 takes another patient temperature reading (from sensor 86) and/or another fluid temperature reading (from sensor 56) and re-performs the loop(s). The specific loop(s) used, as noted previously, depends upon whether thermal control unit 22 is operating in the manual mode or automatic mode.

Figure 5:
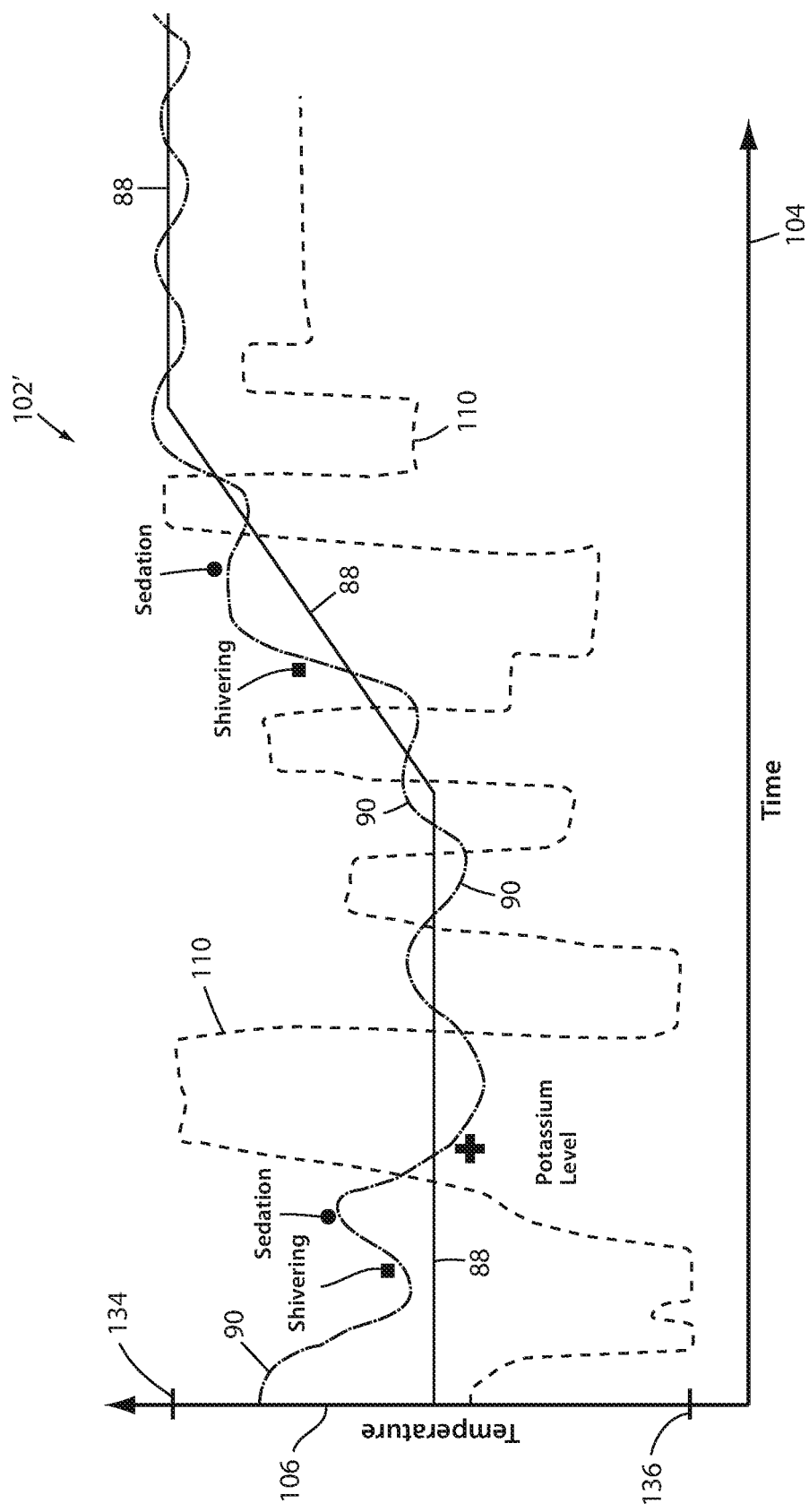
FIG. 5 is another illustrative graph displayable on the user interface of the thermal control unit showing a patient's actual temperature, the patient's target temperature, and a plurality of events.
Figure 6:
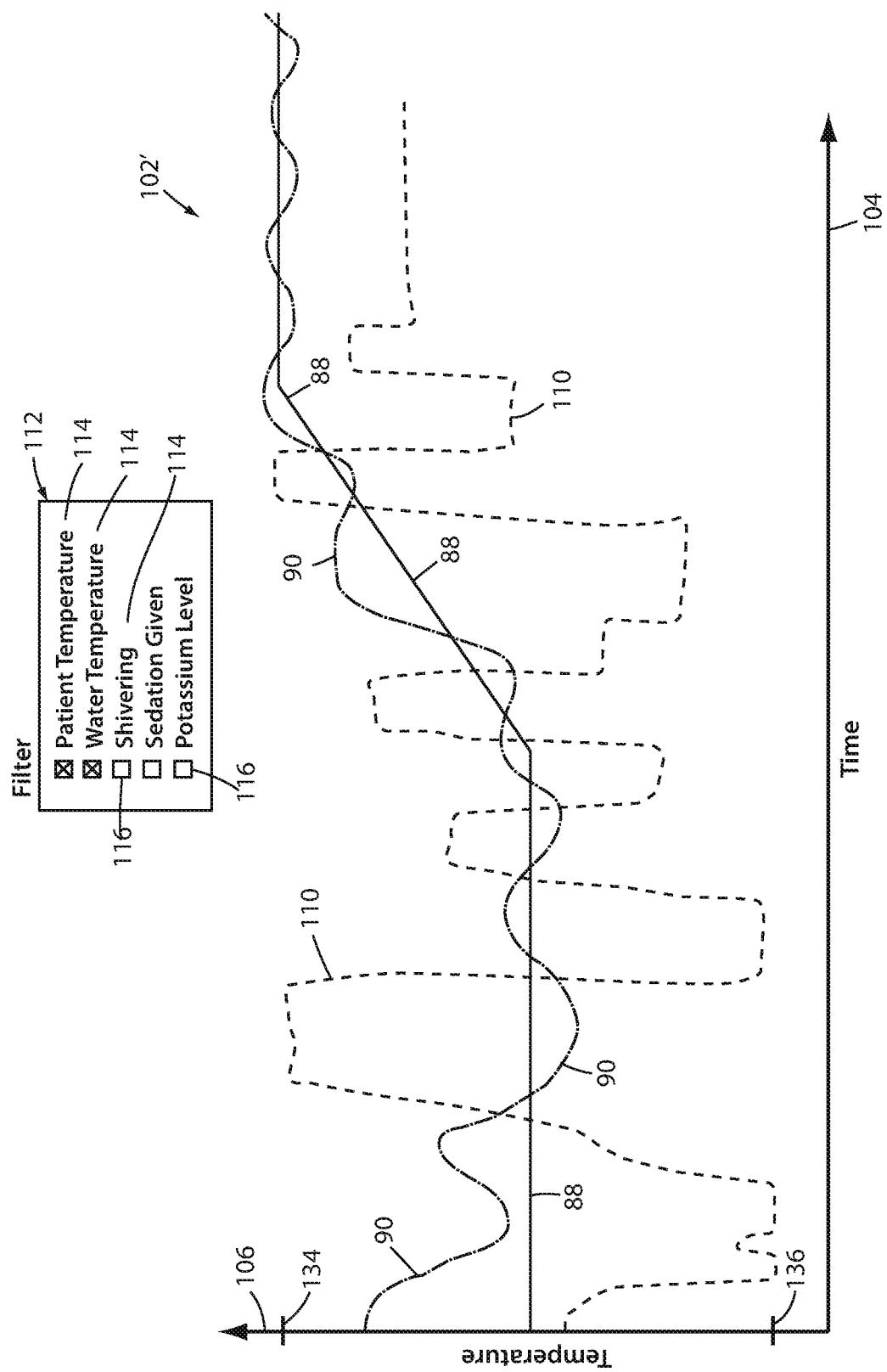
FIG. 6 is the graph of FIG. 5 displayed after a user has activated a filter function for certain patient events.

It will also be understood by those skilled in the art that the output of any control loop used by thermal control unit 22 may be limited such that the temperature of the fluid delivered to thermal pads 24 never strays outside of a predefined maximum and a predefined minimum. Examples of such a predefined maximum temperature 134 and predefined minimum temperature 136 are shown in FIGS. 5 and 6. Minimum temperature 136 is designed as a safety temperature may be set to about four degrees Celsius, although other temperatures may be selected. The predefined maximum temperature 134 is also implemented as a safety measure and may be set to about forty degrees Celsius, although other values may be selected.

In the embodiment shown in FIG. 3, thermal control unit 22 also includes a reservoir valve 96 that is adapted to selectively move fluid reservoir 32 into and out of line with circulation channel 36. Reservoir valve 96 is positioned in circulation channel 36 between air remover 70 and valve 72, although it will be understood that reservoir valve 96 may be moved to different locations within circulation channel 36. Reservoir valve 96 is coupled to circulation channel 36 as well as a reservoir channel 98. When reservoir valve 96 is open, fluid from air remover 70 flows along circulation channel 36 to pump 34 without passing through reservoir 32 and without any fluid flowing along reservoir channel 98. When reservoir valve 96 is closed, fluid coming from air remover 70 flows along reservoir channel 98, which feeds the fluid into reservoir 32. Fluid inside of reservoir 32 then flows back into circulation channel 36 via valve 72. Once back in circulation channel 36, the fluid flows to pump 34 and is pumped to the rest of circulation channel 36 and thermal pads 24 and/or bypass line 64. In some embodiments, reservoir valve 96 is either fully open or fully closed, while in other embodiments, reservoir valve 96 may be partially open or partially closed. In either case, reservoir valve 96 is under the control of controller 60.

Thermal control unit 22 also includes a reservoir temperature sensor 100. Reservoir temperature sensor 100 reports its temperature readings to controller 60. When reservoir valve 96 is open, the fluid inside of reservoir 32 stays inside of reservoir 32 (after the initial drainage of the amount of fluid needed to fill circulation channel 36 and thermal pads 24). This residual fluid is substantially not affected by the temperature changes made to the fluid within circulation channel 36 as long as reservoir valve 96 remains open. This is because the residual fluid that remains inside of reservoir 32 after circulation channel 36 and thermal pads 24 have been filled does not pass through heat exchanger 40 and remains substantially thermally isolated from the circulating fluid. Two results flow from this: first, heat exchanger 40 does not need to expend energy on changing the temperature of the residual fluid in reservoir 32, and second, the temperature of the circulating fluid in circulation channel 36 will deviate from the temperature of the residual fluid as the circulating fluid circulates through heat exchanger 40.

Controller 60 utilizes a temperature control algorithm to control reservoir valve 96 that, in some embodiments, is the same as the temperature control algorithm 160 disclosed in commonly assigned U.S. patent application Ser. No. 62/577,772 filed on Oct. 27, 2017, by inventors Gregory Taylor et al. and entitled THERMAL SYSTEM WITH MEDICATION INTERACTION, the complete disclosure of which is incorporated herein by reference. In other embodiments, controller 60 utilizes a different control algorithm. In still other embodiments, thermal control unit 22 is modified to omit reservoir valve 96, reservoir channel 98, and reservoir temperature sensor 100. Thermal control unit 22 may also be modified such that reservoir 32 is always in the path of circulation channel 36. Still other modifications are possible.

FIG. 4 illustrates one example of a thermal therapy graph 102 that may be displayed by controller 60 on display 80 of user interface 76. Graph 102 is displayable at any time during a thermal therapy session implemented using thermal control unit 22, as well as any time after such a thermal therapy session is complete. That is, controller 60 records the data shown in graph 102 and makes it available for display on display 80 not only during a thermal therapy session, but also after a thermal therapy session.

Thermal therapy graph 102 includes an X-axis 104 that corresponds to time and a Y-axis 106 that corresponds to temperature. Thermal therapy graph 102 shows a history of a patient's actual temperature readings 90 compared to a patient target temperature 88. Thermal therapy graph 102 also includes a plurality of event icons 108 that are positioned at locations along the X-axis 104 corresponding to the times at which the events associated with event icons 108 occurred. For example, event icon 108a corresponds to a patient shivering event. The location of icon 108a along X-axis 104 represents the time at which the shivering occurred. In some embodiments, thermal control unit 22 is adapted to automatically detect the patient shivering and to place event icon 108a on graph 102 without any user intervention. At least one method by which thermal control unit 22 can automatically detect patient shivering is disclosed in commonly assigned U.S. patent application Ser. No. 62/425,813 filed Nov. 23, 2016, by inventors Gregory Taylor et al. and entitled THERMAL SYSTEM, the complete disclosure of which is incorporated herein by reference. Other methods of shivering detection may also be used.

In addition to, or in lieu of, the automatic detection of shivering, thermal control unit 22 may be adapted to allow a user to manually enter data indicating that a patient experienced shivering, including a time when the shivering occurred. In this manner, a user may either directly insert an icon 108 onto graph 102 or may input data into thermal control unit 22 via user interface 76 that specifies that a shivering event took place and the time of the event. In response, controller 60 records the data internally within a memory inside of thermal control unit 22 and displays shivering event icon 108a on graph 102 whenever graph 102 is displayed on display 80.

User interface 76 of thermal control unit 22 is also adapted to display other types of event icons on thermal therapy graph 102. Event icon 108b, for example, corresponds to a sedation event. That is, at the time of event icon 108b along the X-axis shown in FIG. 4, the patient was administered a sedative. Data indicating a sedation event has occurred is input by a user into thermal control unit 22 and controller 60, in response thereto, saves the data and displays event icon 108b on graph 102.

As another example, event icon 108c indicates a patient transfer event. The patient transfer event refers to an event where the patient was transferred to thermal control unit 22 from another thermal control unit, which may be another thermal control unit of the same type as thermal control unit 22, or it may be a thermal control unit of a different type (e.g. a portable thermal control unit, a thermal control unit with a different thermal capacity or other characteristics, etc.). The patient transfer event corresponding to patient transfer event icon 108c is detected either manually or automatically. When done so automatically, data indicating the transfer event may be received from the previous thermal control unit or it may be detected by means on board thermal control unit 22. When received from another thermal control unit, the data indicative of the transfer event (as well as the data shown in FIG. 4 that precedes the transfer event) may be communicated in any of the manners disclosed in commonly assigned U.S. patent application Ser. No. 15/616,574 filed Jun. 7, 2017, by inventors Gregory Taylor et al. and entitled THERMAL CONTROL SYSTEM, the complete disclosure of which is incorporated herein by reference. Other manners of receiving the data may, of course, be used. When the patient transfer event data is detected manually, a user of thermal control system 20 enters data into thermal control unit 22 via user interface 76 indicating the transfer event.

FIG. 4 also illustrates a plurality of additional event icons 108d, 108e, 108f, and 108g. It will be understood by those skilled in the art that the particular number of event icons 108 and their placement on thermal therapy graph 102 will vary from patient to patient according to the specific thermal therapy applied to that particular patient. It will also be understood that other events besides shivering, sedation, and patient transfer may be indicated on graph 102. One such additional event is the administration of a paralytic to the patient. Another event is the administration of yet another type of drug. Still other events include, but are not limited to, the following: adjustment, relocation, cleaning, and/or replacement of one or more thermal pads 24 on the patient; adjustment, relocation, cleaning, and/or replacement of a temperature sensor 86; changing of a setting on thermal control unit 22 (e.g. a rate of heating or cooling, a range of acceptable fluid temperature, etc.); performance of a maintenance task associated with the thermal control unit; detection of an error and/or a patient alert event (e.g. a low potassium level, an elevated blood pressure, a low blood pressure, a low oxygen level, etc.); and/or flushing a patient's body adjacent a temperature sensor.

In some embodiments of thermal control unit 22, controller 60 is also programmed to allow a user to input customized event data. The data, including a time associated with the data, is input using user interface 76t. Controller 60 then displays an event icon 108 on graph 102 at a time location corresponding to the input time data. The customized event icon 108 may include a name or identifier associated with it that is dictated by the user, or it may include a different type of identifier, or no identifier at all.

As can be seen in FIG. 4, each event icon 108 is shaped and/or sized differently according to the type of event it corresponds to. Thus, the shivering event icons 108*a*, 108*d*, and 108*f* are square shaped; the sedation event icons 108*b*, 108*e*, and 108*g* are circle shaped; and the patient transfer event 108*c* is triangle shaped. Although not illustrated, each type of event icon 108 may also be differently colored according to its type. If other types of event icons 108 are displayed on a graph 102 for a particular patient's thermal therapy session, those event icons 108 may be shaped and/or colored in still other manners according to their type.

Additional data beyond an event type and time may also be input into thermal control unit 22 and/or generated internally by thermal control unit 22 for one or more of the event icons 108. In some embodiments, the additional data is viewable by a user after touching or pressing on display 80 (when implemented as a touch screen) in the area of the icon 108. For any of the event icons 108 related to the administration of a drug, such additional data includes one or more of the following: a more precise time of administration, an identification of the particular drug administered, the amount of the drug given, an identification of who administered the drug, a method of administration, and/or other information. For a shivering event, touching a corresponding event icon 108 causes controller 60 to display on display 80 further information about the shivering event, such as, but not limited to, the length of time of the shivering, an indication of the degree of shivering (e.g. a Bedside Shivering Assessment Scale (BSAS) number), a graph of the shivering vibrations as detected, for example, by an accelerometer or other sensor positioned on or near the patient, and/or other information about the shivering. For a patient transfer event, touching a corresponding event icon 108 causes controller 60 to display on display 80 further information about the transfer event, such as, but not limited to, the location of the transfer, an identification of the previously used equipment, and an identification of any previous settings used prior to the transfer. For customized events, touching a corresponding event icon causes controller 60 to display additional information that is available regarding the event associated with the customized event icon 108. The user can select which of the additional information is to be viewed and input configuration data into thermal control unit 22 so that controller 60 only displays the selected additional information.

FIGS. 5-6 illustrate another example of a thermal therapy graph 102'. Thermal therapy graph 102' represents an illustrative set of patient temperature readings 90, patient target temperatures 88, and fluid temperatures 110 that might be generated during a thermal therapy session using thermal control system 20. Fluid temperatures 110 are generated from outlet temperature sensor 56. The patient temperature readings 90, patient target temperatures 88, and fluid temperatures 110 in FIGS. 5 and 6 are the same. The difference between the two figures is the addition of a plurality of event icons 108 in graph 102' of FIG. 5 and the removal of those event icons 108 in graph 102' of FIG. 6. This difference illustrates a display filtering feature that is incorporated into some embodiments of thermal control unit 22.

More specifically, FIG. 6 illustrates a display control window 112 that is displayed on display 80 along with graph 102'. Display control window 112 identifies a plurality of display parameters 114. The display parameters 114 illustrated in FIG. 6 include patient temperature, water (fluid) temperature, shivering, sedation administration, and a patient's low potassium level. Other display parameters may, of course, be added to control window 112. Next to each display parameter 114 is a check box 116 that, when selected by a user, causes controller 60 to display on thermal therapy graph 102' the corresponding display parameter. When the check box 116 is not selected by a user, then the corresponding display parameter 114 is not shown by controller 60 on thermal therapy graph 102'. Display control window 112 and check boxes 116 therefore act together to provide a filtering function for the information displayable on display 80.

Thus, in the example of FIG. 6, it can be seen that the display parameters 114 corresponding to patient temperature and fluid temperature are checked, while the display parameters 114 corresponding to shivering, sedation, and low potassium are not checked. As a result of this selection, controller 60 displays graph 102' with the patient temperature readings 90 and fluid temperature readings 110 shown thereon, but does not include on graph 102' any event icons 108 corresponding to shivering, sedation, and/or low potassium levels. In the example shown in FIG. 5, in contrast, the user has selected all of the display parameters 114 and controller 60 therefore displays, in addition to the patient temperatures 90 and fluid temperature 110, event icons 108 corresponding to patient shivering, sedation, and low potassium levels.

Although not shown in FIG. 5, display control window 112 may also be displayed in that view. Indeed, in some embodiments, an icon on graph 102' (not shown) may be included that, when toggled, causes display control window 112 to alternatively be displayed and not displayed on display 80. Alternatively, or additionally, another control of user interface 76, such as, but not limited to, a dedicated control 82, may control the selective displaying of control window 112. The selection and deselection of check boxes 116 of control window 112 allows a user to selectively declutter the information contained on graph 102' and/or customize the information of interest to a particular clinician.

Figure 7:
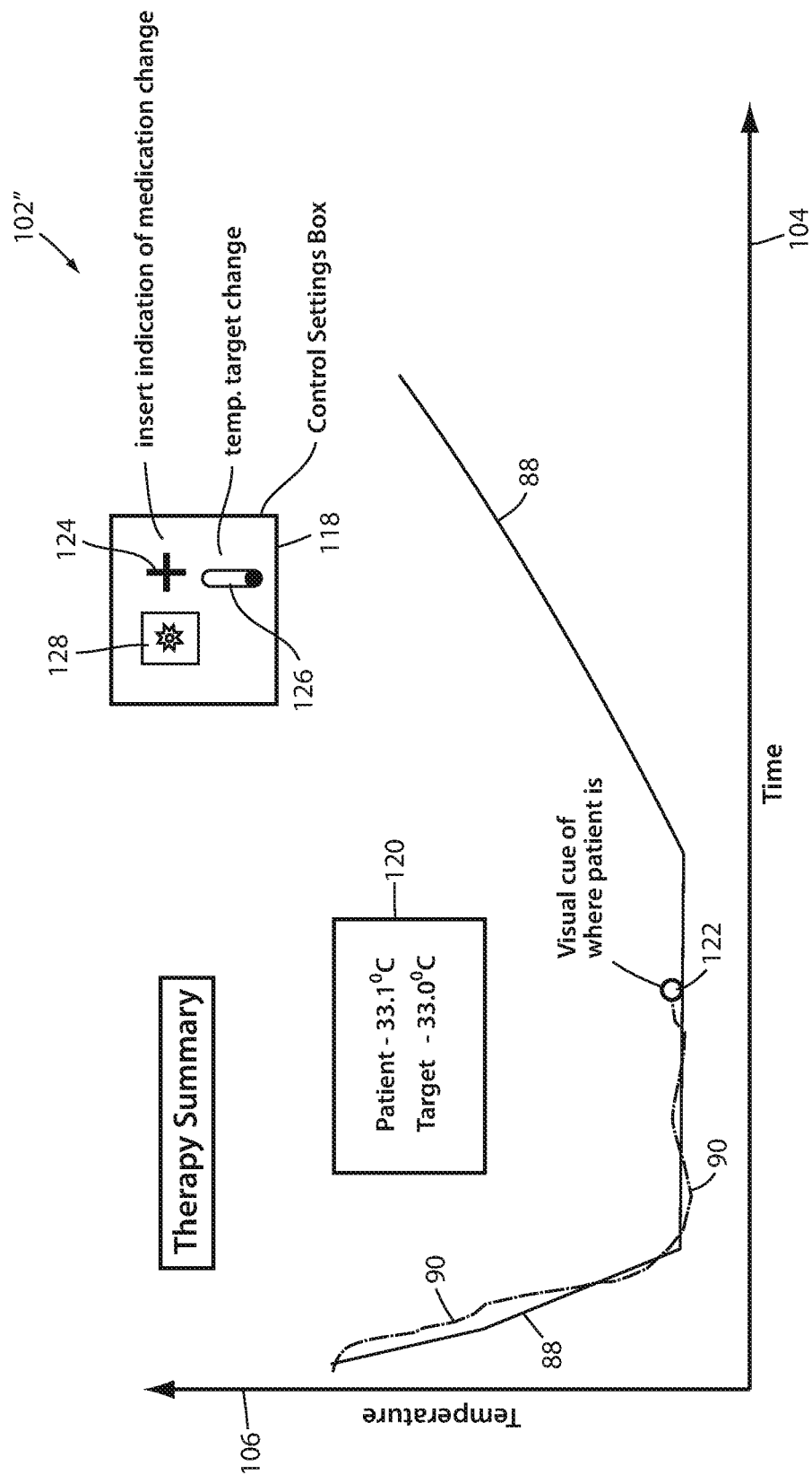
FIG. 7 is another illustrative graph displayable on the user interface of the thermal control unit showing a patient's progress during a thermal therapy session, as well as a user-selectable control box.

FIG. 7 illustrates another example of a thermal therapy graph 102". Thermal therapy graph 102" includes a number of additional features that may be displayed on graphs 102 and/or 102'. These features include a control window 118, a current value window 120, and a current location indicator 122. Control window 118 includes one or more controls for entering information into thermal control unit 22 and/or for controlling the manner in which information is displayed on display 80. These controls include a medication control 124 and a patient target temperature 126. Control window 118 also includes a settings control 128.

Medication control 124 is pressed by a user when the user wishes to input information into thermal control unit 22 about a medication administered to the patient undergoing thermal therapy. In some embodiments, when medication control 124 is pressed, a window appears in which data regarding the medication can be input, such as the type of medication, the amount, the time, etc. After the data is input, controller 60 displays a medication icon 108 on thermal therapy graph 102" in the location corresponding to the time the medication was administered (assuming the check box 116 corresponding to that medication has not been unchecked).

Patient target temperature control 126 is pressed by a user when the user wishes to enter and/or change the patient target temperature 88 for the patient. In some embodiments, when patient target temperature control 126 is pressed, a window appears in which the target temperature and corresponding times for the target temperature can be input. In other embodiments, a user is able to set the patient target temperature by drawing with his or her finger (or stylus, or other touch-screen writing device) a line or set of lines, a curve or a set of curves, or one or more other shapes on graph 102" that define the patient target temperature 88 for the time periods corresponding to the drawn line(s), curve(s) and/or other shape(s). Thus, the line segments in FIG. 7 corresponding to the patient target temperature 88 can be input into thermal control unit 22 by a user drawing the shape shown therein after pressing on target temperature control 126.

Current value window 120 of FIG. 7 displays one or more current values regarding the thermal therapy session being applied to a patient using thermal control system 20. In the example shown in FIG. 7, these current values include the current patient temperature (as measured by patient temperature sensor 86) and the current patient target temperature 88, as input by a user via user interface 76. These are merely two examples of the type of information displayable in current value window 120. Additional examples include, but are not limited to, any one or more of the following: the current fluid temperature, current patient data (e.g. potassium levels, blood pressure, heart rate, respiration rate, oxygen levels, etc.), a current power level of heat exchanger 40, a current flow rate of the circulating fluid, and other data regarding the operation of thermal control unit 22.

Thermal therapy graph 102" also includes current location indicator 122 (FIG. 7). Current location indicator 122 indicates where along time axis 104 the current thermal therapy session has progressed to. Current location indicator 122 may be shaped and/or colored in any manner that provides an easy visual indication to a user of where the thermal therapy is in relation to the time axis 104 and the patient target temperature 88.

Settings control 128, when pressed or otherwise activated by a user, brings up a window (not shown) that allows a user to control various settings regarding the display of information on display 80, including, but not limited to, settings regarding the thermal therapy graph 102". In some embodiments, settings control 128 is selected in order to bring up display control window 112 (FIG. 6). In some embodiments, settings control 128 is also selected in order to change the size, color, contrast, and/or other settings regarding the data displayed on display 80 and/or graph 102".

Figure 8:
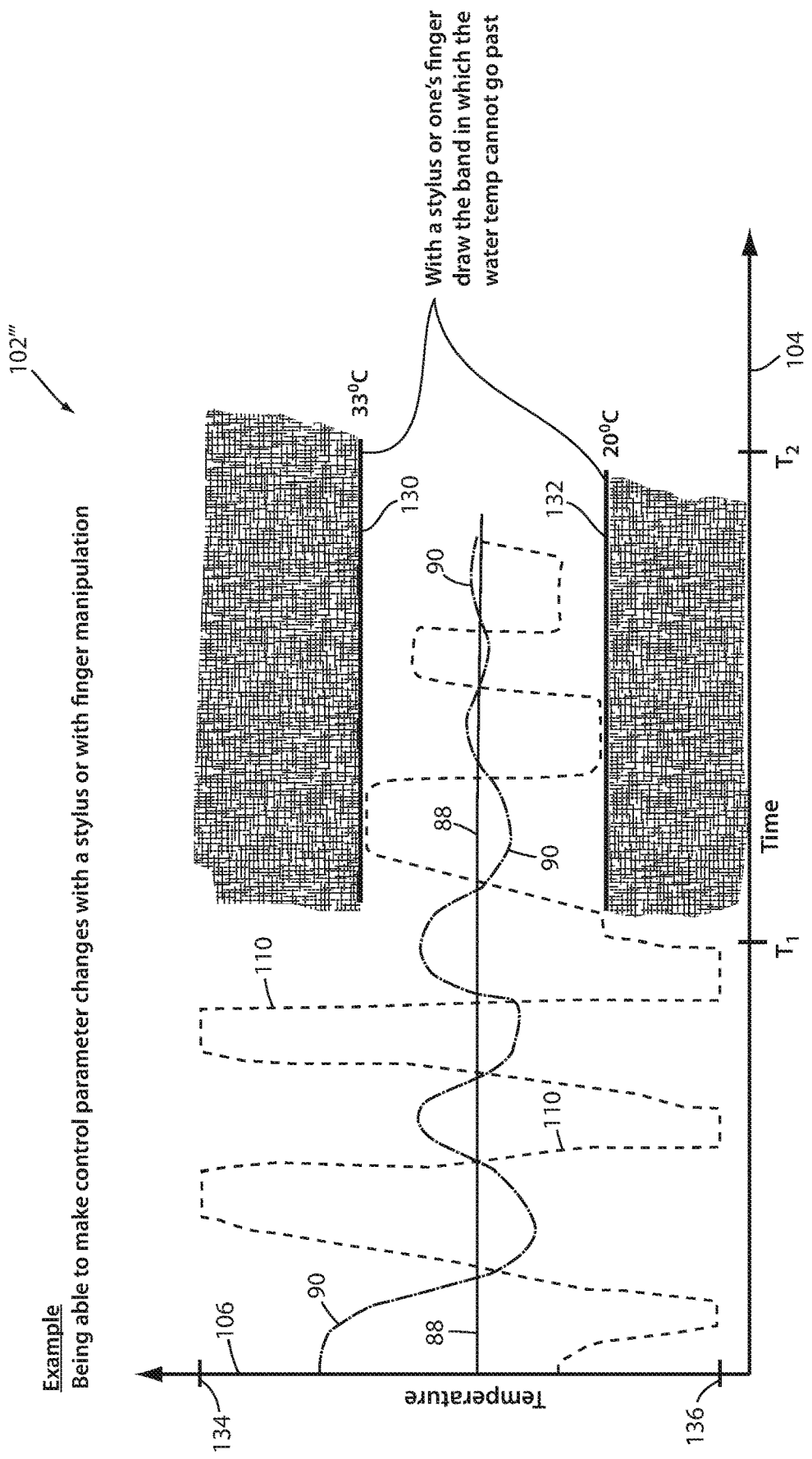
FIG. 8 is another illustrative graph displayable on the user interface of the thermal control unit showing maximum and minimum permissible fluid temperatures selectable by a user.

FIG. 8 illustrates another example of a thermal therapy graph 102'''. Thermal therapy graph 102''' illustrates a fluid temperature control feature that may be included with thermal control unit 22 and that may be incorporated into any of the thermal therapy graphs 102, 102', and/or 102". Thermal therapy graph 102" includes a maximum permissible fluid temperature setting 130 and a minimum permissible fluid temperature setting 132. Maximum permissible fluid temperature setting 130 refers the maximum permissible temperature of the circulating fluid delivered to thermal pads 24. Minimum permissible fluid temperature setting 132 refers to the minimum permissible temperature of the circulating fluid delivered to thermal pads 24.

Thermal control unit 22 includes, as noted previously, a default maximum permissible fluid temperature setting 134 and a default minimum permissible fluid temperature setting 136 (FIGS. 5, 6, & 8). User interface 76, however, is configured to allow a user to change these default maximum and/or minimum temperature settings 134 and 136. Further, user interface 76 is configured to allow a user to specify the time period during which these default maximum and/or minimum temperatures settings 134 and/or 136 are to be changed. As can be seen in the example of FIG. 8, the user has set maximum permissible fluid temperature 130 and minimum permissible fluid temperature 132 for the time period between $T_1$ and $T_2$. In the times outside of the time period between $T_1$ and $T_2$, the maximum and minimum permissible fluid temperatures are set by the default values 134 and 136.

Although FIG. 8 illustrates maximum and minimum permissible fluid temperatures 130 and 132 as horizontal lines, it will be understood that either or both of these lines can be sloped, angled, or configured however desired by a user. In some embodiments, user interface 76 is configured to allow a user to set temperatures 130 and 132 by simply drawing one or more lines on thermal therapy graph 102''', and/or filling in one or more areas of graph 102'''. In those areas where no such line is drawn or no such area is filled in (if any), the default maximum and minimum temperatures 134 and 136 are followed by controller 60. Still further, in some embodiments, controller 60 is configured such that a user can configure the maximum and/or minimum fluid temperatures 130 and/or 132 not as absolute values, but instead as maximum and minimum temperatures relative to the patient's current temperature. In some embodiments, controller 60 allows a user to configure such relative maximum and minimum temperatures by drawing one or more lines on graph 102'''. In other embodiments, a window is displayed on display 80 allowing a user to enter the desired maximum and/or minimum temperatures relative to the patient's temperature.

When user interface 76 of thermal control unit 22 includes a touch screen display 80, controller 60 is adapted, in at least some embodiments, to allow a user to zoom in on, and zoom out from, any of the data shown in graphs 102. Such zooming in and zooming out is carried out in some embodiments in the same way a conventional smart phone operates. For example, the pinching of a users fingers closer together on the touch screen causes controller 60 to zoom out; and the expanding of a users fingers farther apart on the touch screen 80 causes controller 60 to zoom in. Alternatively, or additionally, double tapping on the touch screen display will cause controller 60 to enlarge (zoom in on) the information currently being displayed. Further, in some embodiments, the information displayed is shown in one or more windows that may be resized, moved, and/or opened and closed via the user's fingers interacting with the touch screen display 80.

Figure 9:
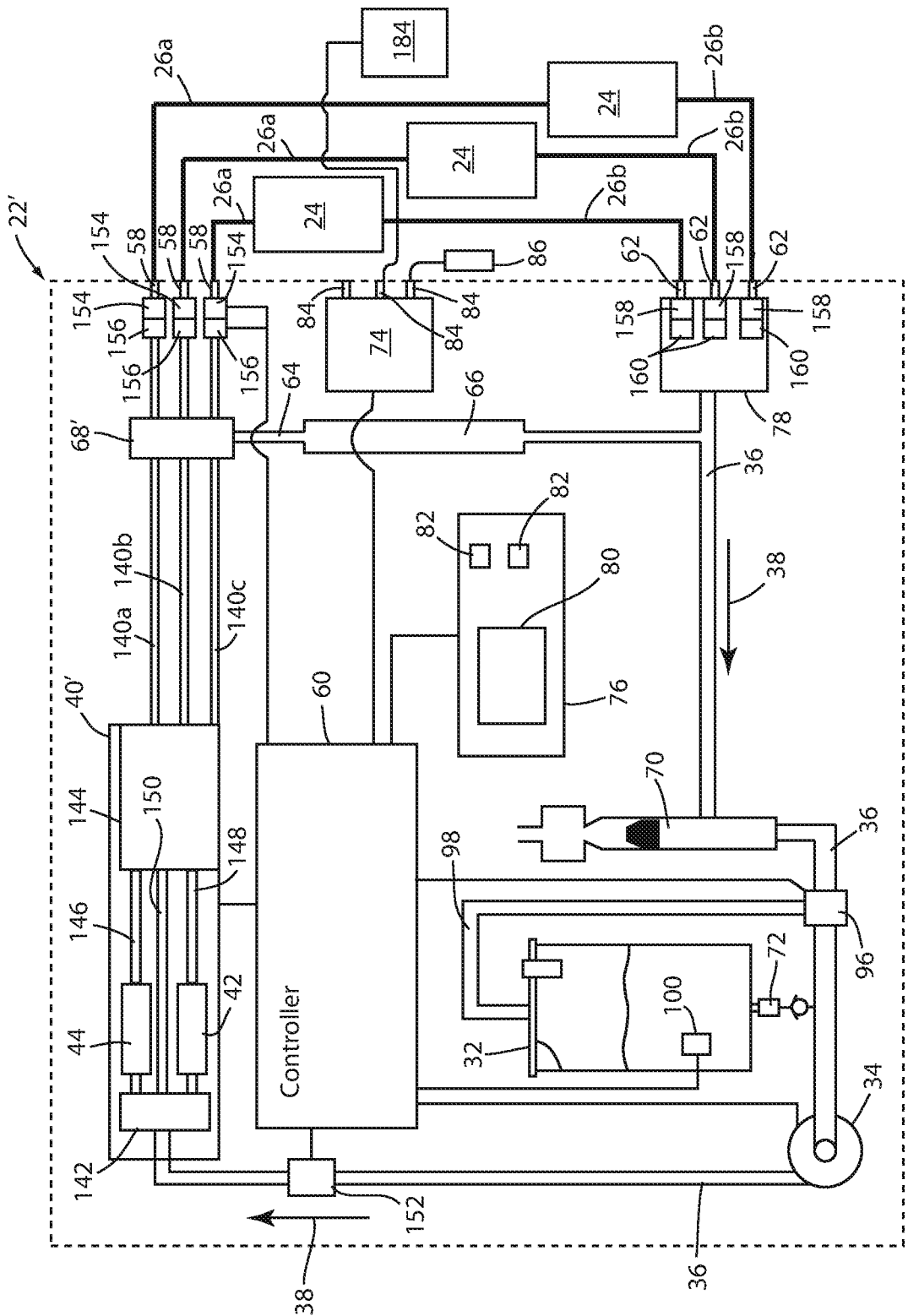
FIG. 9 is a block diagram of an alternative embodiment of a thermal control system according to another aspect of the present disclosure.

FIG. 9 illustrates an alternative embodiment of a thermal control unit 22'. Those elements of thermal control unit 22' that are the same as thermal control unit 22 are labeled with the same reference number and, unless explicitly mentioned otherwise below, operate in the same manner as described with respect to thermal control unit 22. Those elements of thermal control unit 22' that are new are provided with a new reference number, and those elements of thermal control unit 22' that are similar but modified from thermal control unit 22 are provided with the same reference number followed by a prime (') symbol.

Thermal control unit 22' of FIG. 9 differs from thermal control unit 22 in that thermal control unit 22' is adapted to independently control the temperature of the fluid that is delivered to each of the three outlet ports 58. That is, heat exchanger 40' includes three fluid outlets 140a, 140b, and 140c, which are supplied with temperature-controlled fluid by heat exchanger 40', and the temperature of the fluid in each outlet 140a, 140b, and/or 140c may be different from the temperature in one or both of the other outlets 140. Each outlet 140a, 140b, and 140c, after passing through a triple bypass valve 68', is coupled to one of the fluid outlet ports 58 of thermal control unit 22'.

Heat exchanger 40' is able to deliver fluid with independently controlled temperatures by using a set of inlet valves 142 and a set of outlet valves 144. Inlet valves 142 divide the incoming fluid into one or more of three possible paths through heat exchanger 40'. These three paths include a heating path 146, a cooling path 148, and a neutral path 150. Heating path 146 passes through a heater 44'; cooling path 148 passes through a chiller 42', and neutral path 150 does not pass through either a heater or a chiller. Each path 146, 148, and 150 feeds into outlet valves 144 which, like inlet valves 142, are under the control of controller 60. Controller 60 controls the outlet valves 144 such that the heated fluid from path 146, the cooled fluid from path 148, and the unchanged fluid from path 150 are mixed in the proper proportions to deliver fluid to each of the outlets 140 at each of the desired temperatures.

Controller 60 controls the inlet and outlet valves 142 and 144 based on the incoming fluid temperature, which is sensed by temperature sensor 152. Controller 60 uses the output from temperature sensor 152, along with the target temperature for each fluid outlet 140a, 140b, and 140c to determine how much fluid to direct along each of the paths 146, 148, and 150 and how to mix the fluid from each path, via outlet valves 144, such that the fluid delivered to each outlet 140a, b, and c matches the target temperature for that outlet.

By delivering fluid with independently controlled temperatures to each of the outlet ports 58, thermal control unit 22' is able to provide different levels of heating and/or cooling to the individual thermal pads 24 applied to a patient 28. In this manner, for example, fluid of a first temperature might be delivered to the thermal pad 24 in contact with the patient's torso, while fluid of a second temperature might be delivered to the thermal pads 24 in contact with the patient's thighs. Alternatively, fluid of different temperatures might be delivered to all three thermal pads 24. Still other combinations of temperatures for the thermal pads 24 are also possible.

Thermal control unit 22' also differs from thermal control unit 22 in that it includes a plurality of flow control valves or restrictors 154. Each restrictor 154 is positioned in the fluid path of one of the three outlet ports 58. Restrictors 154 are under the control of controller 60 and allow controller 60 to control the amount of fluid that is output from outlet ports 58. Restrictors 154 therefore allow controller 60 to not only independently control the temperature of the fluid delivered to each thermal pad 24, but also to independently control the amount of fluid delivered to each thermal pad 24.

In the illustrated embodiment of FIG. 9, thermal control unit 22' also includes an outlet temperature sensor 156 for each of the outlet ports 58. These may be included in order to allow controller 60 to use positive feedback for the temperature control of each fluid outlet 140a-c. These may also be included in order for controller 60 to calculate the Q value (or heat quantity) that is delivered to each thermal pad 24, or absorbed by each thermal pad 24, as will be discussed in greater detail below.

Thermal control unit 22' also differs from thermal control unit 22 in that it includes individual inlet temperature sensors 158 and individual flow meters 160 positioned inside, or in line with, inlet manifold 78. Each inlet temperature sensor 158 measure the temperature of the fluid returning from a corresponding thermal pad 24 and reports the temperature to controller 60. Each flow meter 160 measures the flow rate of the fluid returning from a corresponding thermal pad 24 and reports the measured flow rate to controller 60. Controller 60 uses the individual temperatures and flow rates for purposes discussed in more detail below, such as the calculation of Q values for each thermal pad 24 and for feedback purposes (e.g. flow meters 160 may be used as closed loop feedback for controlling restrictors 154).

Thermal control unit 22' includes a user interface 76 that is adapted to display information regarding one or more thermal therapy sessions, as well as to control any aspect of thermal control unit 22'. In some embodiments, user interface 76 is adapted to display any of the graphs 102, as wells as to include any of the display functionality, discussed previously with respect to thermal control unit 22. Further, because thermal control unit 22' is adapted to individually control thermal therapy pads 24, controller 60 of thermal control unit 22' is adapted to display individual graphs 102 for each of the thermal pads 24. Alternatively, or additionally, controller 60 may be adapted to display a single graph 102 that shows the measured fluid temperatures for each of the thermal pads 24, or the target fluid temperatures for each of the thermal pads 24, or a combination (e.g. average) of the fluid temperatures for the multiple thermal pads 24. The display of the multiple fluid temperature readings can be selectively enabled and disabled via a display filtering function, such as via a display control window 112 adapted to list display parameters 114 and check boxes 116 corresponding to the various fluid temperatures.

Figure 10:
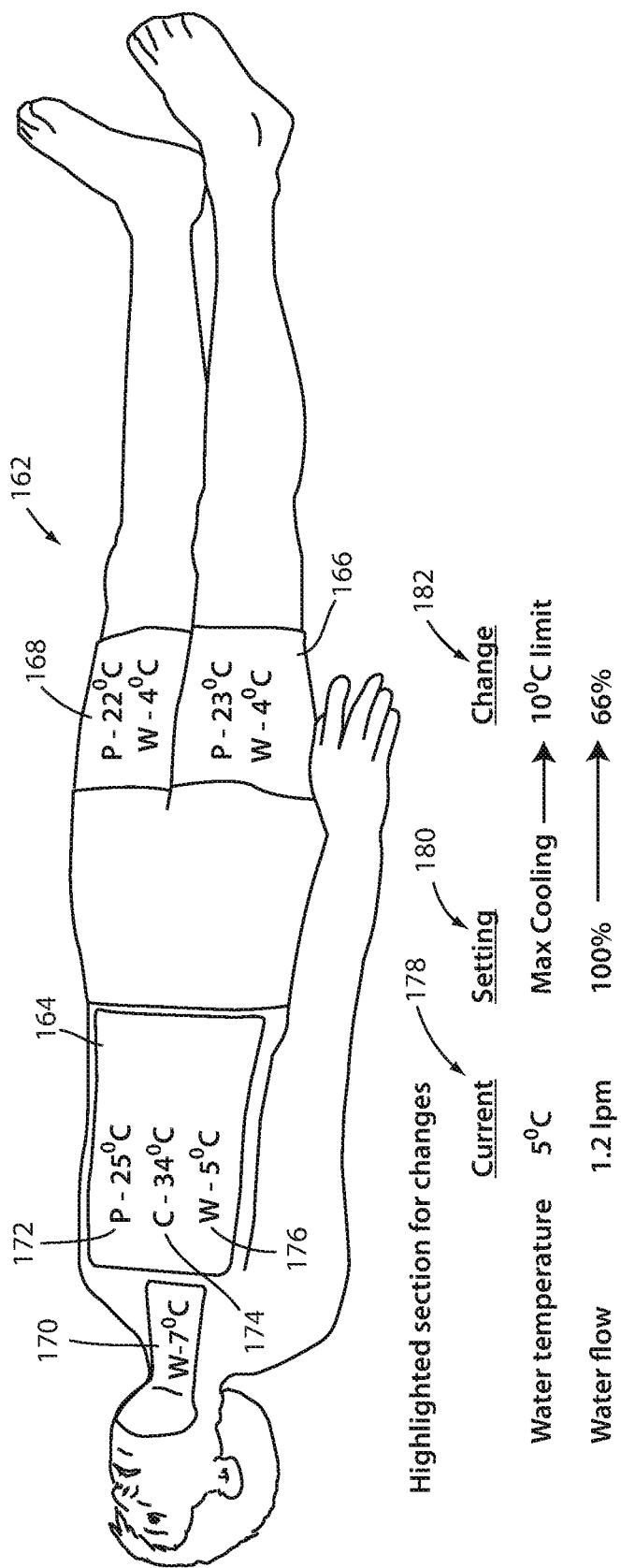
FIG. 10 is an illustrative graphic displayable on the user interface of the thermal control unit of FIG. 10 showing a human body image with multiple zones, including a set of information pertaining to each of the zones.

In at least one embodiment, user interface 76 of thermal control unit 22' is adapted to display an image 162 of a human body, such as the image 162 shown in FIG. 10. Image 162 is representative of a patient 28 undergoing thermal treatment using thermal control unit 22'. Image 162 includes a torso zone 164, a right thigh zone 166, a left thigh zone 168, and a neck zone 170. Torso zone 164 corresponds to a thermal pad 24 wrapped around a patient's torso, and right and left thigh zones 166 and 168 correspond to thermal pads 24 wrapped around the patient's right and left legs, respectively. Neck zone 170, which may be omitted, corresponds to an esophageal heat transfer device that, in some embodiments, receives temperature-controlled fluid from thermal control unit 22'.

For each of the zones 164-170 shown on image 162, controller 60 displays a set of information corresponding to that particular zone. In the example of FIG. 10, controller 60 displays with torso zone 164 a peripheral temperature 172, a core temperature 174, and a fluid temperature 176. Peripheral temperature 172 corresponds to a temperature reading taken in the torso region of the patient that is skin based, or otherwise representative of the temperature of the periphery of the patient's torso. In some embodiments, one or more temperature sensors are incorporated into the thermal pad 24 that is wrapped around the patient's torso and the temperature sensors are positioned in contact with the patient's skin, but thermally insulated from the fluid being circulated through the thermal pads.

Although other designs may be used, some suitable examples thermal pads incorporating temperature sensors that may be used for detecting peripheral temperature 172 are found in commonly assigned U.S. patent application Ser. No. 62/425,813 filed Nov. 23, 2016, by inventors Gregory Taylor et al. and entitled THERMAL SYSTEM, as well as commonly assigned U.S. patent application Ser. No. 15/675,066 filed Aug. 11, 2017, by inventor James K. Galer and entitled THERMAL SYSTEM, the complete disclosures of both of which are hereby incorporated by reference in their entirety herein. Regardless of whether the peripheral temperature sensor(s) are incorporated into a thermal pad 24 or not, the outputs from the temperature sensor(s) are fed to controller 60. In some embodiments, the sensor outputs are fed to controller 60 via cables coupled from the temperature sensors to patient temperature input ports 84. It will be understood that thermal control unit 22' can include more patient temperature input ports 84 than the three shown in FIG. 10.

Core temperature 174 of FIG. 10 refers to the core temperature of the patient as measured by patient temperature sensor 86. Patient temperature sensor 86 may be a conventional temperature sensor that is positioned in the patient's esophagus, rectum, or other location where temperature readings are indicative of the core temperature of the patient. Fluid temperature 176 of FIG. 10 refers to the temperature of the fluid delivered to the thermal pad 24 and may be measured by a temperature sensor positioned in the pad, by temperature sensors 156, and/or by a combination of one or more of these and/or other temperature sensors (e.g. a combination of outlet temperature sensors 156 and inlet temperature sensors 158).

In the example shown in FIG. 10, which corresponds to a touch screen implementation of display 80, controller 60 displays additional information about torso zone 164 when a user of thermal control unit 22' touches the torso portion of image 162. Some of this additional information is shown in FIG. 10, although it will be understood that additional and/or alternative information may be displayed besides the particular information shown in FIG. 10. In the example of FIG. 10, controller 60 displays additional information about the fluid temperature and fluid flow in torso zone 164 in response to a user touching the torso portion of image 162. The additional information includes a current reading column 178, a current setting column 180, and a change column 182. Current reading column 178 displays the current readings for each row of parameters displayed on display 80. Thus, in the example, shown in FIG. 10, controller 60 displays the current fluid temperature reading (five degrees Celsius) for torso zone 164 and the current flow rate (1.2 liters per minute) for torso zone 164. The flow reading may originate from the flow meter 160 that is in fluid communication with the torso thermal pad 24, or from another flow sensor.

Current setting column 180 (FIG. 10) displays the current settings for each row of parameters displayed on display 80. In the example of FIG. 10, the current setting for the fluid temperature is "Max Cooling." This means that thermal control unit 22' is using the coldest available fluid (within permissible limits 130-136, as applicable) to cool the patient. In many embodiments, thermal control unit 22' is configured to allow a user to set different levels of cooling that are less than "Max Cooling." Such different levels of cooling use fluid temperatures that differ from the patient's temperature by a smaller magnitude. For example, a "Min Cooling" setting might cause controller 60 to only supply fluid to a thermal pad 24 that had a temperature that was no more than, say, five degrees cooler than the patient's current temperature. Intermediate cooling settings may also be specified. Still further, in some embodiments, the user may specify an actual temperature for the circulating fluid, or a specific Q rate of heat removal or addition.

For the fluid flow, the current setting in the current setting column 180 of FIG. 10 is indicated as 100%. This indicates that the restrictor 154 in fluid communication with the patients' torso thermal pad 24 is completely open and a full amount of fluid is being delivered to that thermal pad 24. If less than a full amount of fluid is desirably delivered to the torso thermal pad, a user can change the setting to any value less than 100%.

Change column 182 allows a user to change the current setting to a different setting. In the example shown in FIG. 10, controller 60 has provided a suggested change for the current setting. For example, controller 60 has suggested changing the "Max Cooling" setting to a "10° C. limit" setting and the 100% flow rate setting to a 66% flow rate setting. It will be understood that there are other values that a user can choose for changing these settings. In some embodiments, a user touches display 80 in the area of the suggested setting change to implement the suggested change. A confirmation window may appear in order to allow the user to confirm the desired setting. If the user wishes to change the setting in a manner other than the one suggested, the user can, in at least some embodiments, touch the area of the current setting and a setting change window (not shown) is displayed on display 80. The setting change window includes a list of settings to choose from and/or it includes one or more fields for a user to enter the desired new setting.

One of the additional items of information that may be displayed on display 80 for a particular zone is a Q value. The Q value refers to the amount of heat being added to, or removed from, the patient via the corresponding thermal pad. This value is calculated, in at least some embodiments, by determining the difference in temperature between the fluid delivered to the corresponding thermal pad 24 and the fluid returned from the corresponding thermal pad, and then multiplying this temperature difference by the flow rate (in mass per unit of time) and the specific heat capacity of the particular type of fluid (such as, but not limited to, water) being used with thermal control unit 22'. The result is the amount of heat energy being delivered per unit of time via that particular thermal pad 24 (when being used to warm the patient) or the amount of heat energy being absorbed per unit of time via that particular thermal pad 24 (when being used to cool the patient). In some embodiments, the total quantity of heat delivered or absorbed during the thermal therapy session may also or alternatively be displayed for each zone.

Controller 60 is configured to display any of the aforementioned information for each of the thermal pads 24 in each of the zones 164, 166, 168, and 170. In the illustrated embodiment, a user simply touches on the area of image 162 corresponding to the particular zone of interest and controller 60 automatically displays the information corresponding to that particular zone. For example, if a user wishes to determine more information about the right thigh zone 166, the user can touch on the right thigh of the human image 162 and controller 60 displays information pertaining to the right thigh zone. In some embodiments, controller 60 is configured to provide the user with the option of viewing one or more graphs, such as any of the graphs 102 discussed above, for each of the zones 164-170. Alternatively, or additionally, controller 60 may be configured to display graphs 102 that combine information from each of the zones into a single graph 102. The combination may be accomplished through averaging, by superimposing data from each zone onto the graph, or by other methods. Still other data may be combined, such as a combined Q value for all of the zones, a combined flow rate, a combined fluid temperature (e.g. an average fluid temperature), etc.

In some embodiments, controller 60 is not configured to display any information regarding neck zone 170 because thermal control system 20 may be implemented without providing any temperature-controlled fluid to the patient's neck region. (Controller 60 may also be configured to omit any of the other zones 164, 166, and 168 if a corresponding thermal pad is not used). When thermal control unit 22' is used to provide temperature-controlled fluid to a patient's neck region, thermal control unit 22' may be fluidly coupled to an esophageal heat transfer device 184 (FIG. 9). One such suitable esophageal heat transfer device 184 is the ensoETM available from Attune Medical of Chicago, Illinois. The ensoETM is inserted into a patient's esophagus and comes into contact with the esophageal mucosa, allowing blood passing through the patient's blood vessels to be cooled or warmed by the temperature-controlled fluid circulating through the ensoETM. Still other types of esophageal thermal transfer devices may be used. Regardless of the specific type, thermal control unit 22' displays the temperature of the fluid delivered to the esophageal thermal transfer device and/or other information about the device.

Although not illustrated in FIG. 9, thermal control unit 22' may be modified to include an additional fluid outlet port 58 and an additional fluid inlet port 62 to provide fluid to, and receive fluid back from, the esophageal heat transfer device 184. Alternatively, one of hoses 26a may be coupled to a divider that divides its fluid flow so as to deliver fluid to both a thermal pad 24 and an esophageal heat transfer device 184 (or to two thermal pads 24, thereby allowing esophageal heat transfer device 184 to have its own dedicated hose 26a coupled to one of the three outlet ports 58). In such an embodiment, one or more of hoses 26b are joined together to receive returning fluid from both a thermal pad 24 and esophageal heat transfer device 184 (or from two thermal pads 24, thereby allowing the esophageal heat transfer device 184 to have its own dedicated return hose 26b coupled to one of the three inlet ports 62).

It will also be understood that any of the thermal control units disclosed herein may be modified to additionally operate in conjunction with one or more auxiliary sensors used to sense one or more non-temperature patient parameters. When so modified, any of the thermal control units disclosed herein may utilize the auxiliary sensors in any of the manners, and using any of the structures and/or algorithms, disclosed in commonly assigned U.S. patent application Ser. No. 62/610,327 filed Dec. 26, 2017, by inventors Gregory S. Taylor et al. and entitled THERMAL SYSTEM WITH PATIENT SENSOR(S), the complete disclosure of which is incorporated herein by reference.

Any of the thermal control units disclosed herein may also or alternatively be modified to incorporate any of the temperature overshoot reduction methods, structures, and/or algorithms disclosed in commonly assigned U.S. patent application Ser. No. 62/610,319 filed Dec. 26, 2017, by inventors Gregory Taylor et al. and entitled THERMAL SYSTEM WITH OVERSHOOT REDUCTION, the complete disclosure of which is incorporated herein by reference. Additionally or alternatively, any of the thermal control units disclosed herein may use any of the data and algorithms disclosed in U.S. patent application Ser. No. 62/610,334 filed Dec. 26, 2017, by inventors Christopher Hopper et al. and entitled THERMAL CONTROL SYSTEM when determining when a patient's core temperature will reach its temperature, and/or when to transition from heating the circulating fluid to cooling the circulating fluid, and vice versa, in order to reduce overshoot. The '334 application is hereby incorporated herein by reference in its entirety.

Various other alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A thermal control unit for controlling a patient's temperature during thermal therapy, the thermal control unit comprising:

a fluid outlet adapted to fluidly couple to a fluid supply line;

a fluid inlet adapted to fluidly couple to a fluid return line;

a circulation channel coupled to the fluid inlet and the fluid outlet;

a pump for circulating fluid through the circulation channel from the fluid inlet to the fluid outlet;

a heat exchanger adapted to add or remove heat from the fluid circulating in the circulation channel;

a fluid temperature sensor adapted to sense a temperature of the fluid;

a patient temperature sensor port adapted to receive patient temperature readings from a patient temperature sensor;

a controller adapted to control the heat exchanger in order to control the patient's temperature; and a user interface comprising a touch screen display adapted to display patient temperature readings on a graph having a time axis and a temperature axis, the user interface also adapted to display an event icon on the graph, the event icon corresponding to an event occurring at an event time and related to the thermal therapy, and the user interface further adapted to display the event icon at a position along the time axis corresponding to the event time, wherein the event is one of the following: a sedation of the patient; a changing of a thermal pad coupled to the fluid supply line and fluid return line; an adjustment of a thermal pad coupled to the fluid supply line and fluid return line; a change in location of the patient temperature sensor; or a flushing of the patient's body adjacent the patient temperature sensor.

2. The thermal control unit of claim 1 wherein both the event icon and the graph are displayed on the touch screen display, and wherein the user interface is adapted to provide further information about the event when the event icon is touched by a user.

3. The thermal control unit of claim 2 wherein the user interface is adapted to allow a user to touch a first location on the graph along the temperature axis to set a maximum permissible temperature of the fluid, and to touch a second location along the temperature axis to set a minimum permissible temperature of the fluid, the controller adapted to control the heat exchanger such that a temperature of the circulating fluid does not exceed the maximum and minimum permissible temperatures.

4. The thermal control unit of claim 1 wherein the controller is further adapted to detect an occurrence of the event and to automatically display the event icon on the graph after detecting the event occurrence.

5. The thermal control unit of claim 1 wherein the user interface is further adapted to display on the graph fluid temperature readings from the fluid temperature sensor and a patient target temperature, as well as at least one of the following: a heart rate of the patient, a respiration rate of the patient, a potassium level of the patient, and a blood pressure of the patient.

6. The thermal control unit of claim 1 wherein:
the fluid outlet and the fluid inlet are adapted to supply and receive, respectively, temperature-controlled fluid for a first zone of a patient's body, and
the thermal control unit further includes a second fluid outlet and a second fluid inlet adapted to supply and receive, respectively, temperature-controlled fluid for a second zone of a patient's body;
the circulation channel is also coupled to the second fluid inlet and the second fluid outlet;
the fluid temperature sensor is an outlet fluid temperature sensor adapted to sense a temperature of the fluid delivered to the fluid outlet and the second fluid outlet;
the thermal control unit further includes a first inlet fluid temperature sensor adapted to sense a temperature of the fluid returning from the fluid inlet;
the thermal control unit further includes a second inlet fluid temperature sensor adapted to sense a temperature of the fluid returning from the second fluid inlet; and
the user interface is further adapted to display a first set of information relating to the patient's first zone and a second set of information relating to the patient's second zone.

7. The thermal control unit of claim 6 wherein the user interface is further adapted to display an image of a human body and locations of the first and second zones on the human body image, and the user interface is adapted to display the first set of information when a user touches the first zone of the human body image on the touch screen and to display the second set of information when the user touches the second zone of the human body image on the touch screen.

8. The thermal control unit of claim 7 wherein the touch screen is adapted to allow a user to control a first thermal therapy parameter associated with the first zone by touching on the first zone of the human body image, and the user interface is further adapted to allow a user to control a second thermal therapy parameter associated with the second zone by touching on the second zone of the human body image, wherein the first thermal therapy parameter is a limit on a temperature of the fluid delivered to the first zone of the patient's body and the second thermal therapy parameter is a limit on a temperature of the fluid delivered to the second zone of the patient's body.

9. The thermal control unit of claim 1 wherein the user interface is adapted to display a plurality of event icons on the graph, and the plurality of event icons includes at least two of the following: a medication delivered to the patient; a sedation of the patient; a changing of a thermal pad coupled to the fluid supply line and fluid return line; an adjustment of a thermal pad coupled to the fluid supply line and fluid return line; a change in location of the patient temperature sensor; or a flushing of the patient's body adjacent the patient temperature sensor.

10. A thermal control unit for controlling a patient's temperature during thermal therapy, the thermal control unit comprising:
a fluid outlet adapted to fluidly couple to a fluid supply line;
a fluid inlet adapted to fluidly couple to a fluid return line;
a circulation channel coupled to the fluid outlet and the fluid inlet;
a pump for circulating fluid through the circulation channel from the fluid inlet to the fluid outlet;
a heat exchanger adapted to add or remove heat from the fluid circulating in the circulation channel;
a fluid temperature sensor adapted to sense a temperature of the fluid;
a patient temperature sensor port adapted to receive patient temperature readings from a patient temperature sensor;
a controller adapted to control the heat exchanger in order to control the patient's temperature; and
a user interface comprising a touch screen display adapted to display patient temperature readings on a graph having a time axis and a temperature axis, the user interface also adapted to display an event icon on the graph, the event icon corresponding to an event occurring at an event time and related to the thermal therapy, and the user interface is further adapted to display the event icon at a position along the time axis corresponding to the event time and at a position along the temperature axis corresponding to a patient temperature reading at the event time;
wherein the event is one of the following: a medication delivered to the patient; a sedation of the patient; a changing of a thermal pad coupled to the fluid supply line and fluid return line; an adjustment of a thermal pad coupled to the fluid supply line and fluid return line; a change in location of the patient temperature sensor, or a flushing of the patient's body adjacent the patient temperature sensor.

11. The thermal control unit of claim 10 wherein the event corresponds to a first type or a second type of event, and the user interface is adapted to display a filter control that, when selected, filters out all events of the first type such that the user interface does not display any event icons for events of the first type, but continues to display all event icons for events of the second type.

12. The thermal control unit of claim 10 wherein:
the fluid outlet and the fluid inlet are adapted to supply and receive, respectively, temperature-controlled fluid for a first zone of a patient's body, and
the thermal control unit further includes a second fluid outlet and a second fluid inlet adapted to supply and receive, respectively, temperature-controlled fluid for a second zone of a patient's body;
the circulation channel is also coupled to the second fluid inlet and the second fluid outlet;
the fluid temperature sensor is an outlet fluid temperature sensor adapted to sense a temperature of the fluid delivered to the fluid outlet and the second fluid outlet;
the thermal control unit further includes a first inlet fluid temperature sensor adapted to sense a temperature of the fluid returning from the fluid inlet;
the thermal control unit further includes a second inlet fluid temperature sensor adapted to sense a temperature of the fluid returning from the second fluid inlet; and
the user interface is further adapted to display a first set of information relating to the patient's first zone and a second set of information relating to the patient's second zone.

13. The thermal control unit of claim 12 wherein the user interface is further adapted to display an image of a human body and locations of the first and second zones on the human body image, and the user interface includes a touch screen adapted to display the first set of information when a user touches the first zone of the human body image on the touch screen and to display the second set of information when the user touches the second zone of the human body image on the touch screen.

14. The thermal control unit of claim 10 wherein the user interface is adapted to display a plurality of event icons on the graph, and the plurality of event icons includes at least two of the following: a medication delivered to the patient; a sedation of the patient; a changing of a thermal pad coupled to the fluid supply line and fluid return line; an adjustment of a thermal pad coupled to the fluid supply line and fluid return line; a change in location of the patient temperature sensor; or a flushing of the patient's body adjacent the patient temperature sensor.

15. The thermal control unit of claim 10 wherein the user interface is further adapted to allow a user to touch a first location on the graph along the temperature axis to set a maximum permissible temperature of the fluid, and the controller is adapted to control the heat exchanger such that a temperature of the circulating fluid does not exceed the maximum permissible temperature during a first time period corresponding to the first location.

16. The thermal control unit of claim 15 wherein the user interface is further adapted to allow a user to touch a second location along the temperature axis to set a minimum permissible temperature of the fluid, the controller adapted to control the heat exchanger such that a temperature of the circulating fluid does not go below the minimum permissible temperature during a second time period corresponding to the second location.

17. The thermal control unit of claim 16 wherein the user interface is further adapted to allow a user to draw a first line on the graph defining a plurality of maximum permissible temperatures for the first time period, and to draw a second line on the graph defining a plurality of minimum permissible temperatures for the second time period, the controller adapted to control the heat exchanger such that the temperature of the circulating fluid does not exceed the plurality of maximum permissible temperatures during the first time period and does not go below the plurality of minimum permissible temperatures during the second time period.

18. The thermal control unit of claim 16 wherein the user interface is further adapted to allow a user to touch a third location on the graph along the temperature axis to set a target temperature for the patient.

19. The thermal control unit of claim 16 wherein the user interface is further adapted to allow a user to draw a first line on the graph defining a plurality of patient target temperatures at a plurality of times, the controller adapted to control the heat exchanger such that the temperature of the patient is controlled to match the plurality of patient target temperatures at the plurality of times.

* * * * *